(12) United States Patent
Kunikata et al.

(10) Patent No.: US 11,162,064 B2
(45) Date of Patent: Nov. 2, 2021

(54) ELECTROCHEMICAL MEASUREMENT DEVICE AND TRANSDUCER

(71) Applicants: JAPAN AVIATION ELECTRONICS INDUSTRY, LIMITED, Tokyo (JP); TOHOKU UNIVERSITY, Miyagi (JP)

(72) Inventors: Ryota Kunikata, Tokyo (JP); Hiroyuki Hayashi, Tokyo (JP); Atsushi Suda, Tokyo (JP); Kosuke Ino, Miyagi (JP); Kumi Inoue, Miyagi (JP); Tomokazu Matsue, Miyagi (JP)

(73) Assignees: JAPAN AVIATION ELECTRONICS INDUSTRY, LIMITED, Tokyo (JP); TOHOKU UNIVERSITY, Miyagi (JP)

( * ) Notice: Subject to any disclaimer, the term of this patent is extended or adjusted under 35 U.S.C. 154(b) by 232 days.

(21) Appl. No.: 16/336,782

(22) PCT Filed: Sep. 20, 2017

(86) PCT No.: PCT/JP2017/033898
§ 371 (c)(1),
(2) Date: Mar. 26, 2019

(87) PCT Pub. No.: WO2018/066358
PCT Pub. Date: Apr. 12, 2018

(65) Prior Publication Data
US 2019/0256816 A1    Aug. 22, 2019

(30) Foreign Application Priority Data

Oct. 6, 2016 (JP) .............................. JP2016-197818

(51) Int. Cl.
*C12M 1/34* (2006.01)
*G01N 27/327* (2006.01)
(Continued)

(52) U.S. Cl.
CPC .............. *C12M 41/46* (2013.01); *C12M 1/00* (2013.01); *C12M 1/34* (2013.01); *C12M 41/32* (2013.01);
(Continued)

(58) Field of Classification Search
None
See application file for complete search history.

(56) References Cited

U.S. PATENT DOCUMENTS

| | | |
|---|---|---|
| 2003/0078483 A1 | 4/2003 | Herve |
| 2012/0160678 A1 | 6/2012 | Suda et al. |

(Continued)

FOREIGN PATENT DOCUMENTS

| | | |
|---|---|---|
| JP | 2000-35412 A | 2/2000 |
| JP | 2007-225425 A | 9/2007 |

(Continued)

OTHER PUBLICATIONS

K. Y. Inoue, et al., "LSI-based amperometric sensor for bio-imaging and multi-point biosensing", Lab on a Chip, 12(18): p. 3481-3490 (Year: 2012).*

(Continued)

*Primary Examiner* — J. Christopher Ball
(74) *Attorney, Agent, or Firm* — Greenblum & Bernstein, P.L.C.

(57) ABSTRACT

An electrochemical measurement device for measuring a chemical substance generated or consumed in a biological sample in a solution includes electrode surfaces, a spacer, and at least one wall plate. The electrode surfaces, the spacer, and the wall plate are arranged on the same flat surface. Each of the electrode surfaces has a diameter $d_{el}$ not more than 80 μm. A height of the spacer has a predetermined value within a range given by $h=21.8(d_{el}+0.8)/(d_{el}+9.7)\pm5$ [μm]. The spacer has a structure in which an enclosed (Continued)

three-dimensional region is not formed by the biological sample, the flat surface, and the spacer while the biological sample is in contact with the spacer. The wall plate has a property of being impervious to a dissolved substance in the solution and has a height not less than the height of the spacer. Two of the electrode surfaces are separated by the wall plate.

24 Claims, 13 Drawing Sheets

(51) Int. Cl.
  *G01N 33/543* (2006.01)
  *G01N 33/487* (2006.01)
  *C12M 1/00* (2006.01)
(52) U.S. Cl.
  CPC ... *G01N 27/3277* (2013.01); *G01N 33/48728* (2013.01); *G01N 33/5438* (2013.01)

(56) References Cited

U.S. PATENT DOCUMENTS

| | | |
|---|---|---|
| 2015/0260675 A1 | 9/2015 | Nakatani et al. |
| 2017/0015971 A1 | 1/2017 | Shunori et al. |
| 2017/0336384 A1 | 11/2017 | Ino et al. |
| 2018/0372676 A1 | 12/2018 | Kunikata et al. |
| 2019/0086356 A1 | 3/2019 | Hayashi et al. |

FOREIGN PATENT DOCUMENTS

| | | |
|---|---|---|
| JP | 6086412 B1 | 3/2017 |
| WO | 2014/073195 A1 | 5/2014 |
| WO | 2015/151395 A1 | 10/2015 |
| WO | 2017/110258 A1 | 6/2017 |

OTHER PUBLICATIONS

Office Action issued in Chinese Counterpart Patent Appl. No. 201780058155.2, dated Aug. 26, 2020, along with an English translation thereof.

Office Action issued in European Patent Office (EPO) Counterpart Patent Appl. No. 17858197.1, dated Jan. 21, 2021.

Kanno et al., "Simulation analysis of positional relationship between embryoid bodies and sensors on an LSI-based amperometric device for electrochemical imaging of alkaline phosphatase activity", Analytical Sciences, Jul. 10, 2015, pp. 715-719.

Sen et al., "LSI-based amperometric sensor for real-time monitoring of embryoid bodies", Biosensors and Bioelectronics, 2013, pp. 12-18.

Ino et al., "Electrochemical device with interdigitated ring array electrodes for investigatng the relationship between cardiomyocyte differentiation from embryonic stem cells and alkaline phosphatase activity", Electrochemisty, 2013, pp. 682-687.

U.S. Appl. No. 15/776,195 to Hiroyuki Hayashi et al., which was filed on May 15, 2018.

Extended European Search Report (EESR) for Application No. EP 17858197.1, dated Oct. 28, 2019.

European Patent Office Summons to attend oral proceedings dated Jul. 8, 2021.

* cited by examiner

ELECTROCHEMICAL MEASUREMENT DEVICE AND TRANSDUCER

TECHNICAL FIELD

The present invention relates to an electrochemical measurement device and a transducer used to electrochemically measuring a chemical substance generated or consumed in a biological sample. The biological sample is (1) a constituent element of a biological body, (2) a collection of constituent elements of a biological body, (3) a biologically-relevant substance [the biologically-relevant substance is a chemical substance present inside a body of an organism, and examples of the biologically-relevant substance include a biopolymer, a constituent element of a biopolymer, or a chemical substance necessary for survival of an organism], or (4) a tangible object including one or more of (1) to (3). Examples of the biological sample include cells, cell aggregates, pieces of tissue, and non-biological tangible objects containing biologically-relevant substances.

BACKGROUND ART

Building of a technology for quantitatively evaluating a chemical substance generated or consumed in a cell contributes significantly not only to development of fundamental biochemistry but also to development of medicine and life science. The technology can be used, for example, for cytoscreening used in cancer screening tests, for quality evaluation of cells for transplantation used in regenerative medicine or immune cell therapies, or as a substitute for experimentation on animals for drug efficacy assessments and toxicity assessments.

However, bioactivities of cells not only vary with the environment surrounding the cells, such as temperature, pH, medium composition, adjacent cell, and extracellular matrix, but also vary over time in response to an external stimulus, such as gene introduction, drug exposure, or application of stress, or a cellular event, such as cell division or cell death.

For this reason, it is important to place cells as a biological sample in an environment as close to an intravital environment as possible while the cells are alive (that is, bioactivities thereof are retained) and further measure, in real time, a chemical substance generated or consumed in the cells in response to an external stimulus or a cellular event in order to evaluate the true nature of a cell actually in work inside a biological body.

One known method for placing cells as a biological sample in an environment close to an intravital environment is a method using, as a biological sample, not a single cell but a cell aggregate (spheroids) which is an aggregate of a plurality of cells and extracellular matrix (ECM) components.

Since many of various bioactivities of cells are developed by an interaction with adjacent cells or ECMs which contact the cells, a cell aggregate is considered to reproduce an intravital environment more faithfully than a single cell.

Examples of a cell aggregate include pancreatic islet cells harvested from the pancreas, fertilized eggs, hepatocyte or neurocyte spheroids obtained by cell culture, and embryoid bodies of embryonic stem (ES) cells.

While cell aggregates used in evaluation of cell activities have diameters that differ depending on the types of constituent cells, the harvest site inside a biological body, culture conditions, and the like, the diameters are about 100 to 600 μm. This is because the number of constituent cells in a small cell aggregate having a diameter of 100 μm or less is too small for a bioactivity specific to the cell aggregate to develop and because oxygen does not diffuse to cells in a cell aggregate central portion in a large cell aggregate having a diameter of 600 μm or more to make cell necrosis likely occur.

As a method for measuring, in real time, a chemical substance generated or consumed in cells, an electrochemical method is used. The electrochemical method uses an electrode (working electrode) for detecting various electrochemical signals from a biological sample. The working electrode is placed in a solution in which a biological sample is to be immersed. Various detection methods are available to accommodate differences in potential control or current control of the working electrode. Controlled potential electrolysis (constant-potential electrolysis) typified by chrono amperometry or cyclic voltammetry is used in measurement associated with metabolic activities of cells or the like because of its high comparability and simplicity of analysis. Controlled potential electrolysis controls the potential of the working electrode as a function of time and detects a value of a current generated in the working electrode.

In electrochemical measurement of a chemical substance generated or consumed in a common cell aggregate, a reaction system which causes a chemical substance having a redox activity to be generated or consumed inside the cell aggregate or at a surface of the cell aggregate in association with substance metabolism of the cell aggregate is set in advance. The chemical substance is oxidized or reduced on a working electrode to generate a current.

Various systems can be designed in accordance with a metabolic system of interest as reaction systems which cause a chemical substance having a redox activity to be generated or consumed in association with substance metabolism of cells. A system using an enzymatic reaction is preferably used for the purpose of detecting, with high sensitivity, a minute amount of metabolic substance.

For example, in an embryoid body which is a cell aggregate produced from mouse ES cells, the amount of alkaline phosphatase (ALP) which is an enzyme present at a cell surface increases or decreases in accordance with a differentiation state.

Electrochemical evaluation of the amount of ALP generated is often performed in order to evaluate the differentiation state of an embryoid body (Non-patent Literature 1). In a system for the evaluation, an embryoid body is put in a solution in which p-aminophenyl phosphate (PAPP) as a substrate is dissolved, and a dephosphorylation reaction of PAPP is facilitated by an ALP enzymatic activity. This results in generation of p-aminophenol (PAP) having a redox activity.

When the concentration of PAPP in the solution is sufficiently high, even if the amount of ALP generated in cells is minute, the amounts of PAP that is a redox-active chemical substance can be accumulated with time by the enzymatic activity of ALP. Consequently, the amount of ALP present can be detected with high sensitivity.

If the above-described electrochemical measurement is to be performed on a single biological sample, a single electrode which is formed on a substrate or is processed in the shape of a probe is generally used as a working electrode. To perform electromechanical measurement on a plurality of biological samples, a plurality of working electrodes are used.

For example, a method called drug screening is used at the time of drug discovery. In drug screening, a plurality of cells are exposed to respective different chemical substances, and changes in bioactivity of the cells are exhaustively evaluated in order to search for a chemical substance which can exert an expected action on a given type of cell (that is, a chemical substance as a candidate for a drug) among a plurality of chemical substances different in structure from one another.

Cell evaluation in drug screening is performed by various analysis methods. When cell evaluation is to be performed by an electrochemical method, a plurality of working electrodes formed on the same substrate are used to simultaneously evaluate a plurality of cells arranged near the working electrodes (multipoint simultaneous electrochemical measurement).

Multipoint simultaneous electrochemical measurement makes a time period required for evaluation much shorter than in a case where evaluation of cells are separately performed. Generally, substrate modification, cell pretreatment, and adjustment of measurement conditions (the composition, pH, temperature, and the like of a measurement solution) are all performed on a per-substrate basis. For this reason, the process of accumulating a plurality of electrodes and a plurality of biological samples on one substrate and collectively performing the pretreatment and the measurement condition adjustment implements saving of a drug to be used, reduction of waste water, and the like and further allows measurement conditions for the biological samples to match up more accurately with one another.

PRIOR ART LITERATURE

Non-Patent Literature

Non-patent Literature 1: M. Sen, et al., "Biosensors and Bioelectronics", 2013, Vol. 48, pp. 12-18

SUMMARY OF THE INVENTION

Problems to be Solved by the Invention

A redox-active chemical substance which is generated in cells spreads radially from the cells into a solution by a diffusion action unless an external special hydrodynamic action is exerted. As a result, part of the generated chemical substance reaches a working electrode and undergoes oxidation and reduction. For this reason, the amount of the chemical substance generated and a diffusion distance of the chemical substance to the working electrode largely affect the amount of current generated in the working electrode. Similarly, a chemical substance consumed in cells moves toward near the cells, where the concentration of the chemical substance is reduced by the consumption, due to a diffusion action.

However, if a working electrode is formed on a substrate and a biological sample is brought closer to the working electrode, the distance between the biological sample and the substrate decreases. Supply of a substrate dissolved in a solution to the biological sample is blocked, and the amount of a chemical substance generated in the biological sample by an enzymatic reaction is smaller than in a case where a biological sample is away from the substrate and is suspended in the solution. Additionally, since the volume of a three-dimensional region between the biological sample and the working electrode is small, most of the generated chemical substance cannot remain in the three-dimensional region and scatters away. The distance from the scattered chemical substance to the working electrode is long, the amount of the chemical substance that reaches the working electrode decreases, and sensitivity lowers (problem 1).

Further, since the surface state of the biological sample is not even, and the biological sample is not a perfect sphere, a straight-line distance between the working electrode and the biological sample is different for every measurement operation. The straight-line distance varies typically by at least several µm each time measurement is performed. For this reason, a diffusion distance of the chemical substance is inconstant, and comparability and reproducibility of measurement lower (problem 2).

When a plurality of biological samples are to be simultaneously evaluated by a plurality of working electrodes on a substrate, a value of a current flowing through each working electrode is most affected by the amount of a chemical substance generated or consumed in a nearest biological sample but is also affected to no small extent by the amount of the chemical substance generated or consumed in a different biological sample in the distance (the problem of crosstalk). To accurately detect the amount of the chemical substance generated or consumed in each biological sample, a state in which a value of a current flowing through a working electrode reflects only substance metabolism of a single biological sample is most preferable. For this reason, to reduce the influence of a biological sample located in the distance, a wide interval between biological samples and a wide interval between working electrodes for evaluating the biological samples need to be secured. Widening of the interval between working electrodes, however, increases the area of the substrate, on which the working electrodes are formed. This invites a rise in substrate cost. For example, if a substrate on which working electrodes are to be formed is manufactured as part of an large scale integration (LSI) chip on an upper surface of the LSI chip by a semiconductor manufacturing technology, an increase in the size and the cost of the LSI chip is inevitable (problem 3).

In Non-patent Literature 1, the amounts of chemical substances are measured by a plurality of working electrodes on a substrate, which has problems 1, 2, and 3 described above.

Problem 1 described above can be fixed by using not a working electrode on a substrate but a probe-like working electrode (a probe electrode). Since a tip of a probe electrode is generally much smaller than a biological sample, the probe electrode and a probe electrode support do not block supply of a dissolved substance in a solution to the biological sample more greatly than a working electrode on a substrate. A position of a probe electrode relative to a biological sample is generally finely controlled on the order of µm by a manipulator. For this reason, problem 2 described above is also fixed.

However, position control of a probe electrode requires expensive equipment, such as a manipulator and a microscope system for observing a probe tip position. Probe electrodes are often broken by inexperienced users.

When evaluation of a plurality of biological samples is to be performed, since movement of a probe by a manipulator needs considerable time, promptness of measurement and identicalness of biological samples in measurement conditions are greatly impaired.

In view of the above-described circumstances, an object of the present invention is to provide an electrochemical measurement device and a transducer used for electrochemical measurement which are higher in sensitivity, comparability, and reproducibility than ever before.

Means to Solve the Problems

According to the invention of claim 1, in an electrochemical measurement device including a plurality of working electrodes, each of the plurality of working electrodes including an electrode surface supplying or receiving electrons to or from a chemical substance generated or consumed in a biological sample in a solution to cause an oxidation-reduction reaction, all of the electrode surfaces have diameter dimensions $d_{el}$ not more than 80 μm and are arrayed on one flat surface, a spacer is provided in a solution well containing the solution and the biological sample, the spacer having a profile surface at a distance $h_1$ in a direction perpendicular to the one flat surface, the distance $h_1$ satisfying $$h_1 = 21.8(d_{el}+0.8)/(d_{el}+9.7) \pm 5 \ [\mu m],$$

the spacer inhibiting the biological sample from entering a region on a side with the one flat surface of the profile surface and allowing a dissolved substance in the solution to diffuse, and a wall plate is provided between the two electrode surfaces adjacent to each other, the wall plate extending to cross a line connecting centers of the two electrode surfaces, having a height not less than a height of the spacer from the one flat surface, and being impervious to the dissolved substance in the solution.

According to the invention of claim 2, in an electrochemical measurement device including a plurality of working electrodes, each of the plurality of working electrodes including an electrode surface supplying or receiving electrons to or from a chemical substance generated or consumed in a biological sample in a solution to cause an oxidation-reduction reaction, all of the electrode surfaces have diameter dimensions $d_{el}$ not more than 80 μm and are arrayed on one flat surface, a spacer is provided in a solution well containing the solution and the biological sample, the spacer having an inverse-cone-shaped profile surface at a distance $h_2$ in a direction perpendicular to the one flat surface, the distance $h_2$ being dependent on a distance m in a direction parallel to the one flat surface from a center of the closest electrode surface and satisfying $$h_2 = [(1.05d_{el}+6.89)m]^{1/2} - 0.48d_{el} - 2.38 \pm 5 \ [\mu m],$$

the spacer inhibiting the biological sample from entering a region on a side with the one flat surface of the profile surface and allowing a dissolved substance in the solution to diffuse, and a wall plate is provided between the two electrode surfaces adjacent to each other, the wall plate extending to cross a line connecting centers of the two electrode surfaces, having a height not less than a maximum height of the spacer from the one flat surface, and being impervious to the dissolved substance in the solution.

According to the invention of claim 3, in the invention of claim 1 or 2, the electrode surfaces are arrayed in a configuration in which a plurality of electrode rows are arranged in a second direction orthogonal to a first direction, each of the plurality of electrode rows having the plurality of the electrode surfaces which are arranged in a straight line in the first direction, and the wall plate is provided to extend in the first direction between the electrode rows adjacent to each other.

According to the invention of claim 4, in the invention of any one of claims 1 to 3, the spacer is composed of a group of pillar structures which extend in the direction perpendicular to the one flat surface and stand at intervals less than 100 μm.

According to the invention of claim 5, in the invention of any one of claims 1 to 3, the spacer is composed of a porous structure having a pore diameter less than 100 μm.

According to the invention of claim 6, in an electrochemical measurement device including a plurality of working electrodes, each of the plurality of working electrodes including an electrode surface supplying or receiving electrons to or from a chemical substance generated or consumed in a biological sample in a solution to cause an oxidation-reduction reaction, all of the electrode surfaces have diameter dimensions $d_{el}$ not more than 80 μm and are arrayed on one flat surface, on which x-y orthogonal coordinates are defined, such that x coordinates of centers of the at least two electrode surfaces are different from each other, and a plurality of wall plates are provided to be arrayed at intervals less than 100 μm in an x direction on the one flat surface where the electrode surfaces are arrayed, each of the plurality of wall plates extending in a y direction, having a height $h_3$ satisfying $$h_3 = 21.8(d_{el}+0.8)/(d_{el}+9.7) \pm 5 \ [\mu m],$$

and being impervious to a dissolved substance in the solution.

According to the invention of claim 7, in the invention of claim 6, the height $h_3$ of at least one of two of the wall plates, distances in the x direction of which from a center of one of the electrode surfaces are smallest and second smallest, changes along the y direction so as to be minimal at a y coordinate equal to a y coordinate of the center of the electrode surface.

According to the invention of claim 8, in the invention of claim 6, the heights $h_3$ of two of the wall plates which extend on two outer sides of one of the electrode surfaces and are parallel to each other without a different one of the wall plates sandwiched between the two wall plates change along the y direction so as to be minimal at y coordinates equal to a y coordinate of a center of the electrode surface.

According to the invention of claim 9, in the invention of claim 6, an x coordinate of at least one of two of the wall plates, distances in the x direction of which from a center of one of the electrode surfaces are smallest and second smallest, changes locally along the y direction such that the distance in the x direction from the center of the electrode surface is maximal at a y coordinate equal to a y coordinate of the center of the electrode surface.

According to the invention of claim 10, in the invention of claim 6, an x coordinate of a first wall plate which is one of the wall plates, a distance in the x direction of which from a center of one of the electrode surfaces is smallest, changes locally along the y direction such that the distance in the x direction from the center of the electrode surface is maximal at a y coordinate equal to a y coordinate of the center of the electrode surface, and an x coordinate of a second wall plate which is a different one of the wall plates which is adjacent to the first wall plate across the center of the electrode surface changes locally along the y direction such that a distance in the x direction from the center of the electrode surface is maximal at a y coordinate equal to the y coordinate of the center of the electrode surface.

According to the invention of claim 11, in the invention of any one of claims 6 to 10, a tall wall plate is further provided between at least one combination of two x-direction adjacent electrode surfaces, each of the at least one combination of the two x-direction adjacent electrode surfaces being a combination of two of the electrode surfaces, x coordinates of centers of the two electrode surfaces being different from each other, a different one of the electrode surfaces which has an x coordinate intermediate between the x coordinates being not present, the tall wall plate extending in the y direction to cross a line segment connecting centers of the two electrode surfaces over a whole of a width of the tall wall plate, having a height more than the heights of the wall plates, and being impervious to the dissolved substance in the solution.

According to the invention of claim 12, in an electrochemical measurement device including a plurality of working electrodes, each of the plurality of working electrodes including an electrode surface supplying or receiving electrons to or from a chemical substance generated or consumed in a biological sample in a solution to cause an oxidation-reduction reaction, all of the electrode surfaces have diameter dimensions $d_{el}$ not more than 80 μm and are arrayed on one flat surface, on which x-y orthogonal coordinates are defined, in a configuration in which a plurality of electrode rows are arranged in an x direction, each of the plurality of electrode rows having one or more of the electrode surfaces which are arranged in a y direction such that x coordinates of centers of all of the one or more electrode surfaces match up, and a plurality of wall plates are provided to be arrayed at intervals less than 100 μm in the x direction on the one flat surface where the electrode surfaces are arrayed, the plurality of wall plates extending in the y direction, having heights $h_4$, and being impervious to a dissolved substance in the solution, the heights $h_4$ being dependent on a distance m in the x direction from a center of one of the electrode surfaces which belongs to the electrode row that is closest in the x direction and satisfying $$h_4 = [(1.05 d_{el} + 6.89)m]^{1/2} - 0.48 d_{el} - 2.38 \pm 5 \, [\mu m]$$

and changing gradually.

According to the invention of claim 13, in the invention of claim 12, the height $h_4$ of at least one of one or more of the wall plates which each extend to cross a line segment connecting a first end point and a second end point over a whole or part of a width of the wall plate changes along the y direction so as to be minimal at a y coordinate equal to a y coordinate of a center of one of the electrode surfaces, the first end point being not a relatively farther one of a point 300 μm away in one direction of the x direction from the center of the electrode surface and a point at a distance which is one-half of a distance to an x coordinate of a center of the electrode surface which belongs to the electrode row that is adjacent in the one direction, the second end point being not a relatively farther one of a point 300 μm away in the other direction of the x direction from the center of the electrode surface and a point at a distance which is one-half of a distance to an x coordinate of a center of the electrode surface which belongs to the electrode row that is adjacent in the other direction.

According to the invention of claim 14, in the invention of claim 13, the heights $h_4$ of all of one or more of the wall plates which each extend to cross the line segment over the whole of the widths of the wall plates change along the y direction so as to be minimal at y coordinates equal to the y coordinate of the center of the electrode surface.

According to the invention of claim 15, in the invention of any one of claims 12 to 14, a tall wall plate is further provided between at least one combination of the electrode rows which are adjacent to each other in the x direction, the tall wall plate extending in the y direction at an x coordinate intermediate between x coordinates of centers of the electrode surfaces which belong to the two electrode rows, having a height more than a maximum height of the wall plates, and being impervious to the dissolved substance in the solution.

According to the invention of claim 16, in a transducer s in which a solution well capable of containing a solution and a biological sample immersed in the solution is mounted on an LSI chip, and a plurality of working electrodes that each include an electrode surface supplying or receiving electrons to or from a chemical substance generated or consumed in the biological sample in the solution to cause an oxidation-reduction reaction are provided on the LSI chip, all of the electrode surfaces have diameter dimensions $d_{el}$ not more than 80 μm and are arrayed on one flat surface, a spacer is provided in the solution well, the spacer having a profile surface at a distance $h_1$ in a direction perpendicular to the one flat surface, the distance $h_1$ satisfying $$h_1 = 21.8(d_{el} + 0.8)/(d_{el} + 9.7) \pm 5 \, [\mu m],$$

the spacer inhibiting the biological sample from entering a region on a side with the one flat surface of the profile surface and allowing a dissolved substance in the solution to diffuse, and a wall plate is provided between the two electrode surfaces adjacent to each other, the wall plate extending to cross a line connecting centers of the two electrode surfaces, having a height not less than a height of the spacer from the one flat surface, and being impervious to the dissolved substance in the solution.

According to the invention of claim 17, in a transducer in which a solution well capable of containing a solution and a biological sample immersed in the solution is mounted on an LSI chip, and a plurality of working electrodes that each include an electrode surface supplying or receiving electrons to or from a chemical substance generated or consumed in the biological sample in the solution to cause an oxidation-reduction reaction are provided on the LSI chip, all of the electrode surfaces have diameter dimensions $d_{el}$ not more than 80 μm and are arrayed on one flat surface, a spacer is provided in the solution well, the spacer having an inverse-cone-shaped profile surface at a distance $h_2$ in a direction perpendicular to the one flat surface, the distance $h_2$ being dependent on a distance m in a direction parallel to the one flat surface from a center of the closest electrode surface and satisfying $$h_2 = [(1.05 d_{el} + 6.89)m]^{1/2} - 0.48 d_{el} - 2.38 \pm 5 \, [\mu m],$$

the spacer inhibiting the biological sample from entering a region on a side with the one flat surface of the profile surface and allowing a dissolved substance in the solution to diffuse, and a wall plate is provided between the two electrode surfaces adjacent to each other, the wall plate extending to cross a line connecting centers of the two electrode surfaces, having a height not less than a maximum height of the spacer from the one flat surface, and being impervious to the dissolved substance in the solution.

According to the invention of claim 18, in the invention of claim 16 or 17, the electrode surfaces are arrayed in a configuration in which a plurality of electrode rows are arranged in a second direction orthogonal to a first direction, each of the plurality of electrode rows having the plurality of the electrode surfaces which are arranged in a straight line in the first direction, and the wall plate is provided to extend in the first direction between the electrode rows adjacent to each other.

According to the invention of claim 19, in the invention of any one of claims 16 to 18, the spacer is composed of a group of pillar structures which extend in the direction perpendicular to the one flat surface and stand at intervals less than 100 μm.

According to the invention of claim 20, in the invention of any one of claims 16 to 18, the spacer is composed of a porous structure having a pore diameter less than 100 μm.

According to the invention of claim 21, in a transducer in which a solution well capable of containing a solution and a biological sample immersed in the solution is mounted on an LSI chip, and a plurality of working electrodes that each include an electrode surface supplying or receiving electrons to or from a chemical substance generated or consumed in the biological sample in the solution to cause an oxidation-reduction reaction are provided on the LSI chip, all of the electrode surfaces have diameter dimensions $d_{el}$ not more than 80 μm and are arrayed on one flat surface, on which x-y orthogonal coordinates are defined, such that x coordinates of centers of at least two of the electrode surfaces are different from each other, and a plurality of wall plates are provided to be arrayed at intervals less than 100 μm in an x direction on the one flat surface where the electrode surfaces are arrayed, each of the plurality of wall plates extending in a y direction, having a height $h_3$ satisfying $$h_3 = 21.8(d_{el}+0.8)/(d_{el}+9.7) \pm 5 \text{ } [\mu m],$$

and being impervious to a dissolved substance in the solution.

According to the invention of claim 22, in the invention of claim 21, the height $h_3$ of at least one of two of the wall plates, distances in the x direction of which from a center of one of the electrode surfaces are smallest and second smallest, changes along the y direction so as to be minimal at a y coordinate equal to a y coordinate of the center of the electrode surface.

According to the invention of claim 23, in the invention of claim 21, the heights $h_3$ of two of the wall plates which extend on two outer sides of one of the electrode surfaces and are parallel to each other without a different one of the wall plates sandwiched between the two wall plates change along the y direction so as to be minimal at y coordinates equal to a y coordinate of a center of the electrode surface.

According to the invention of claim 24, in the invention of claim 21, an x coordinate of at least one of two of the wall plates, distances in the x direction of which from a center of one of the electrode surfaces are smallest and second smallest, changes locally along the y direction such that the distance in the x direction from the center of the electrode surface is maximal at a y coordinate equal to a y coordinate of the center of the electrode surface.

According to the invention of claim 25, in the invention of claim 21, an x coordinate of a first wall plate which is one of the wall plates, a distance in the x direction of which from a center of one of the electrode surfaces is smallest, changes locally along the y direction such that the distance in the x direction from the center of the electrode surface is maximal at a y coordinate equal to a y coordinate of the center of the electrode surface, and an x coordinate of a second wall plate which is a different one of the wall plates which is adjacent to the first wall plate across the center of the electrode surface changes locally along the y direction such that a distance in the x direction from the center of the electrode surface is maximal at a y coordinate equal to the y coordinate of the center of the electrode surface.

According to the invention of claim 26, in the invention of any one of claims 21 to 25, a tall wall plate is further provided between at least one combination of two x-direction adjacent electrode surfaces, each of the at least one combination of the two x-direction adjacent electrode surfaces being a combination of two of the electrode surfaces, x coordinates of centers of the two electrode surfaces being different from each other, a different one of the electrode surfaces which has an x coordinate intermediate between the x coordinates being not present, the tall wall plate extending in the y direction to cross a line segment connecting centers of the two electrode surfaces over a whole of a width of the tall wall plate, having a height more than the heights of the wall plates, and being impervious to the dissolved substance in the solution.

According to the invention of claim 27, in a transducer in which a solution well capable of containing a solution and a biological sample immersed in the solution is mounted on an LSI chip, and a plurality of working electrodes that each include an electrode surface supplying or receiving electrons to or from a chemical substance generated or consumed in the biological sample in the solution to cause an oxidation-reduction reaction are provided on the LSI chip, all of the electrode surfaces have diameter dimensions $d_{el}$ not more than 80 μm and are arrayed on one flat surface, on which x-y orthogonal coordinates are defined, in a configuration in which a plurality of electrode rows are arranged in an x direction, each of the plurality of electrode rows having one or more of the electrode surfaces which are arranged in a y direction such that x coordinates of centers of all of the one or more electrode surfaces match up, and a plurality of wall plates are provided to be arrayed at intervals less than 100 μm in the x direction on the one flat surface where the electrode surfaces are arrayed, the plurality of wall plates extending in the y direction, having heights $h_4$, and being impervious to a dissolved substance in the solution, the heights $h_4$ being dependent on a distance m in the x direction from a center of one of the electrode surfaces which belongs to the electrode row that is closest in the x direction and satisfying $$h_4 = [(1.05d_{el}+6.89)m]^{1/2} - 0.48d_{el} - 2.38 \pm 5 \text{ } [\mu m]$$

and changing gradually.

According to the invention of claim 28, in the invention of claim 27, the height $h_4$ of at least one of one or more of the wall plates which each extend to cross a line segment connecting a first end point and a second end point over a whole or part of a width of the wall plate changes along the y direction so as to be minimal at a y coordinate equal to a y coordinate of a center of one of the electrode surfaces, the first end point being not a relatively farther one of a point 300 μm away in one direction of the x direction from the center of the electrode surface and a point at a distance which is one-half of a distance to an x coordinate of a center of the electrode surface which belongs to the electrode row that is adjacent in the one direction, the second end point being not a relatively farther one of a point 300 μm away in the other direction of the x direction from the center of the electrode surface and a point at a distance which is one-half of a distance to an x coordinate of a center of the electrode surface which belongs to the electrode row that is adjacent in the other direction.

According to the invention of claim 29, in the invention of claim 28, the heights $h_4$ of all of one or more of the wall plates which each extend to cross the line segment over the whole of the widths of the wall plates change along the y direction so as to be minimal at y coordinates equal to the y coordinate of the center of the electrode surface.

According to the invention of claim 30, in the invention of any one of claims 27 to 29, a tall wall plate is further provided between at least one combination of the electrode rows which are adjacent to each other in the x direction, the tall wall plate extending in the y direction at an x coordinate intermediate between x coordinates of centers of the electrode surfaces which belong to the two electrode rows, having a height more than a maximum height of the wall plates, and being impervious to the dissolved substance in the solution.

Effects of the Invention

The present invention allows measurement of a chemical substance generated or consumed in a biological sample in a solution with high sensitivity, comparability, and reproducibility.

DETAILED DESCRIPTION OF THE EMBODIMENTS

Figure 1:
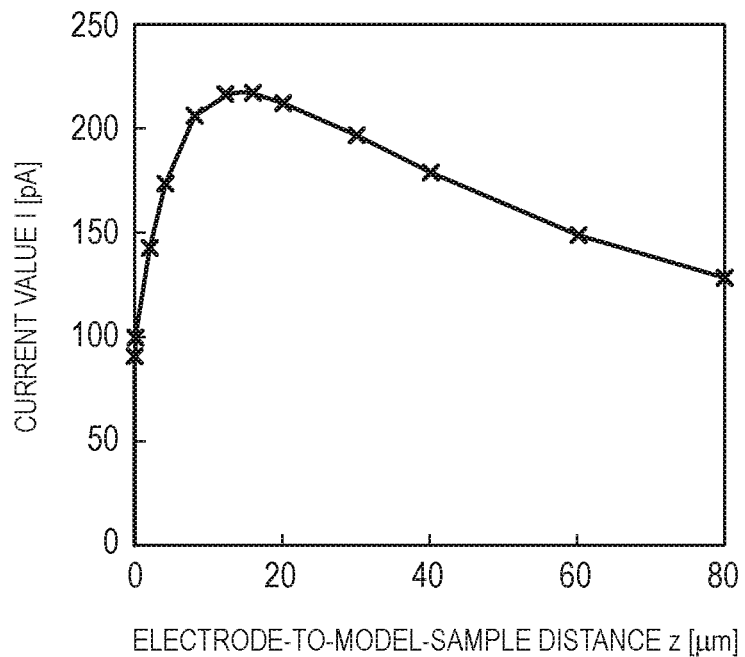
FIG. 1 is a graph showing a relationship between an electrode-to-model-sample distance z and a current value I.

The inventors made an detailed analysis of a relationship between a process of diffusion of a dissolved substance in a solution which is associated with a chemical reaction occurring in a biological sample and a current flowing through an electrode on a substrate in electrochemical measurement. As a result, the inventors found the fact that arranging a biological sample at a given distance determined by an electrode surface diameter and a biological sample diameter away from an electrode surface in a direction perpendicular to the electrode surface and forming a path for free diffusion of a dissolved substance below the biological sample made the amount of current larger and measurement sensitivity higher than in a case where the biological sample was immediately above and close to the electrode surface.

The inventors also found the fact that arranging a biological sample away from an electrode surface in a direction perpendicular to the electrode surface made variability in current value due to the low accuracy of controlling a position of the biological sample relative to the electrode surface smaller than that when the biological sample was immediately above and close to the electrode surface and improved measurement comparability and reproducibility.

Simulation results which have led to the above-described findings will be described below.

In simulations, the simulation software COMSOL Multiphysics (Japanese registered trademark) was used. An embryoid body produced from mouse ES cells was adopted as a model sample. PAP generated by an ALP enzymatic reaction at a surface of the model sample was adopted as a chemical substance to be generated in the model sample. The chemical substance (PAP) generated in the model sample diffuses, reaches an electrode surface of a working electrode, and is oxidized on the electrode surface. At this time, a value of a current generated in the working electrode is detected. The other conditions are as described below.

<Enzymatic Reaction>

At a surface of a model sample, an ALP enzymatic reaction using PAPP that is a dissolved substance in a solution as a substrate progresses, and PAP is generated. A rate v of reaction (generation) for the ALP enzymatic reaction follows Michaelis-Menten equation (1).

$$v = \frac{A_{sp} V_{max} [S]}{K_m + [S]} \quad (1)$$

In equation (1), $A_{SP}$ represents the surface area of the model sample, $V_{max}$ represents a rate of reaction per unit surface area of the model sample when the substrate concentration is infinite, $K_m$ represents the Michaelis constant for the ALP enzymatic reaction, and [S] represents the substrate concentration. Values of $V_{max}$ and $K_m$ were respectively set to $2.65 \times 10^{-7}$ mol/(s·m$^2$) and $1.7 \times 10^{-3}$ mol/L. An initial value of [S] was set to $5.0 \times 10^{-3}$ mol/L.

<Electrode Reaction>

A two-electron oxidation reaction of PAP generated in the model sample progresses on the electrode. An electrode potential was assumed to be sufficiently high for the reaction to be completely diffusion-controlled. A current value I during the reaction follows equation (2).

$$I = \int_{A_{el}} i(x, y) dA_{el} \quad (2)$$

$$i(x, y) = nFD \frac{dc(x, y)}{dz} \quad (3)$$

In equation (3), $i(x,y)$ and $c(x,y)$ respectively represent a current density and the concentration of the chemical substance to be detected, at an arbitrary point $(x,y)$ on a surface of the electrode. $A_{el}$ represents an electrode area, n represents the number of electrons involved in the reaction, F represents the Faraday constant, D represents a diffusion coefficient of the chemical substance to be detected in the solution, and z represents a coordinate in a direction perpendicular to the electrode surface (an x-y plane). n, F, and D were respectively set to 2, $9.64 \times 10^4$ C/mol, and $6.47 \times 10^{-10}$ m$^2$/s. The current value I after 200 seconds since the start of the electrode reaction was shown as a measurement result.

<Others>

Shape of model sample: diameter $d_{sp}$=200 μm, spherical

Shape of electrode surface: diameter $d_{el}$=20 μm, circular

Position of electrode surface: a horizontal distance between central coordinates of the electrode surface and center coordinates $(x,y)$ of the model sample is 0

Distance z: 0 to 80 μm

The present inventors investigated how the current value I resulting from the oxidation reaction of the chemical substance generated in the model sample changed with the distance z between the electrode surface and a lower end of the model sample. FIG. 1 is a graph of a simulation result representing a relationship between the current value I and the distance z.

As seen from FIG. 1, the current value I has a local maximum value at z=16 μm. Thus, it turned out that placing the model sample at an optimum position where a peak current value was obtained made measurement sensitivity much higher than the sensitivity when the distance z was 0 μm. The tendency of the distance z is independent of the electrode diameter $d_{el}$ and the model sample diameter $d_{sp}$.

Further, it is clear from FIG. 1 that a variation in the current value I when the distance z varies near the above-described local maximum value is much smaller than a variation in the current value I when the distance z varies near z=0 μm. If a cell, a cell aggregate, a piece of tissue, or the like is adopted as a biological sample, it is difficult to control the distance z with an accuracy of several μm because unevenness is present at a surface of the biological sample or the shape of the biological sample is not necessarily a spherical shape. However, setting the distance z to a value near the local maximum value can reduce variability in the current value I resulting from the low accuracy of controlling the distance z, resulting in improvements in the accuracy of determining a quantitative relationship between different measurement objects (comparability) and the reproducibility of a measurement result for the same measurement object.

The closer to the local maximum value the distance z is, the larger the improvements in the comparability and the reproducibility becomes. The improvements are especially remarkable when the distance z is within a range where the current value is 90% or more of the peak current value. For this reason, if the distance z is set to a value within the range, potent effects are achieved not only in terms of improving the sensitivity but also in terms of improving the comparability and the reproducibility.

It was found from results of various simulations performed by the inventors that the effective range for the distance z varied significantly depending on measurement conditions, especially the electrode diameter and the biological sample diameter. It is thus necessary to set an electrode having an appropriate diameter and the appropriate distance z in order to evaluate a biological sample having a particular diameter.

However, in the case of biological samples, such as cells, cell aggregates, or pieces of tissue, the diameters of the biological samples vary widely depending on the types and states of cells. Even if the biological samples are harvested from the same site of the same test body or are acquired under the same culture conditions, the diameters of the biological samples vary by several μm to several hundreds of μm. It is unrealistic in terms of cost to check the diameters of all biological samples before measurement and set an appropriate electrode diameter and the appropriate distance z for each biological sample. Additionally, quantitative comparison of measurement results acquired for different electrode diameters and different values of the distance z is extremely difficult.

In order to solve the above-described problems, it is effective to obtain an electrode diameter and a range for the distance z which allow production of potent effects for all biological samples having various diameters within a reasonable range and to measure various biological samples using an electrochemical measurement device with the same configuration.

The inventors obtained electrode diameters and a range for the distance z which achieve high sensitivity, the effect of improving the comparability, and the effect of improving the reproducibility if the diameters of cell aggregates, which are said to more accurately reproduce a bioactivity inside a biological body, vary within the commonly used range of 100 to 600 μm. The procedure for the obtainment will be described below.

Figure 2:
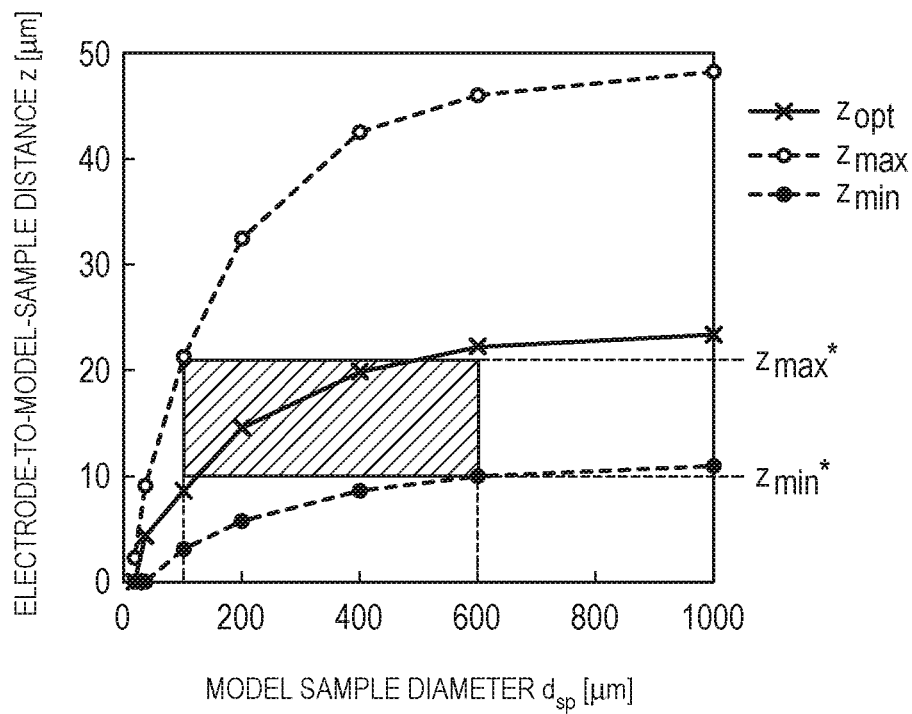
FIG. 2 is a graph showing a relationship between a model sample diameter $d_{sp}$ and an effective range for the electrode-to-sample distance z.

First, the inventors investigated how a lower limit $z_{min}$ and an upper limit $z_{max}$ of an effective range for the distance z changed with the model sample diameter $d_{sp}$ if the electrode diameter $d_{el}$ was 20 μm. FIG. 2 shows a result of the simulation. When the electrode diameter $d_{el}$ is 20 μm and the distance z is not less than $z_{min}$ and not more than $z_{max}$ shown in FIG. 2 for each value of the model sample diameter $d_{sp}$, the current value I is 90% or more of the peak current value ($z_{opt}$ in the drawing represents an optimum value for the distance z which gives the peak current value). Let $z_{max}$* be $z_{max}$ when the model sample diameter $d_{sp}$ is 100 μm and $z_{min}$* be $z_{min}$ when the model sample diameter $d_{sp}$ is 600 μm. If the distance z is within a shaded range in FIG. 2 which has a lower limit of $z_{min}$* and an upper limit of $z_{max}$* when the model sample diameter $d_{sp}$ has a value of 100 to 600 μm, the current value I is 90% or more of the peak current value.

Figure 3:
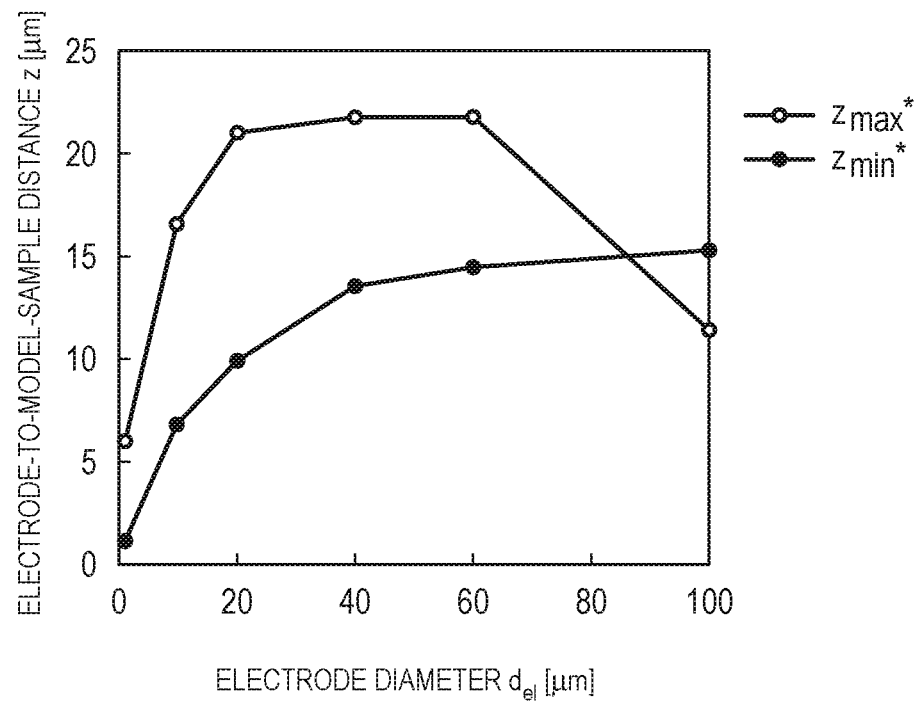
FIG. 3 is a graph showing a relationship between an electrode diameter $d_{el}$ and the effective range for the electrode-to-sample distance z.

The inventors then investigated how $z_{min}$* and $z_{max}$* changed with the electrode diameter $d_{el}$. FIG. 3 shows a result of the simulation. If a value of the electrode diameter $d_{el}$ is within the range of 0 to 80 μm, and the distance z is within the range not less than $z_{min}$* and not more than $z_{max}$* shown in FIG. 3, the above-described potent effects are obtained for biological samples having $d_{sp}$=100 to 600 μm. By fitting operation using a non-linear least-squares method, the range for the distance z is roughly represented by equation (4) that is a function of the electrode diameter $d_{el}$. Thus, the distance z may be set within the range represented by equation (4), where z>0.

$$z = \frac{21.8(d_{el} + 0.8)}{d_{el} + 9.7} \pm 5 [\mu m] \quad (4)$$

As can be seen from FIG. 3, equation (4) cannot be used when the electrode diameter $d_{el}$ is not less than about 80 μm. However, electrochemical measurement on minute biological samples, such as cells, commonly uses an electrode having $d_{el}$=50 μm or less. This is because an S/N ratio of a current value (the ratio between a Faraday current generated by an oxidation-reduction reaction of a chemical substance to be detected and a charging current generated by an electrolyte not to be detected) increases significantly at an electrode having $d_{el}$=50 μm or less. Thus, the distance z can be determined in accordance with equation (4).

The effective range for the distance z can vary depending on the rate v of generation, at which a chemical substance is generated in a biological sample, and the diffusion coefficient D of the chemical substance, in addition to the electrode diameter $d_{el}$ and the biological sample diameter $d_{sp}$. The influences of the parameters, however, are limited.

Figure 4:
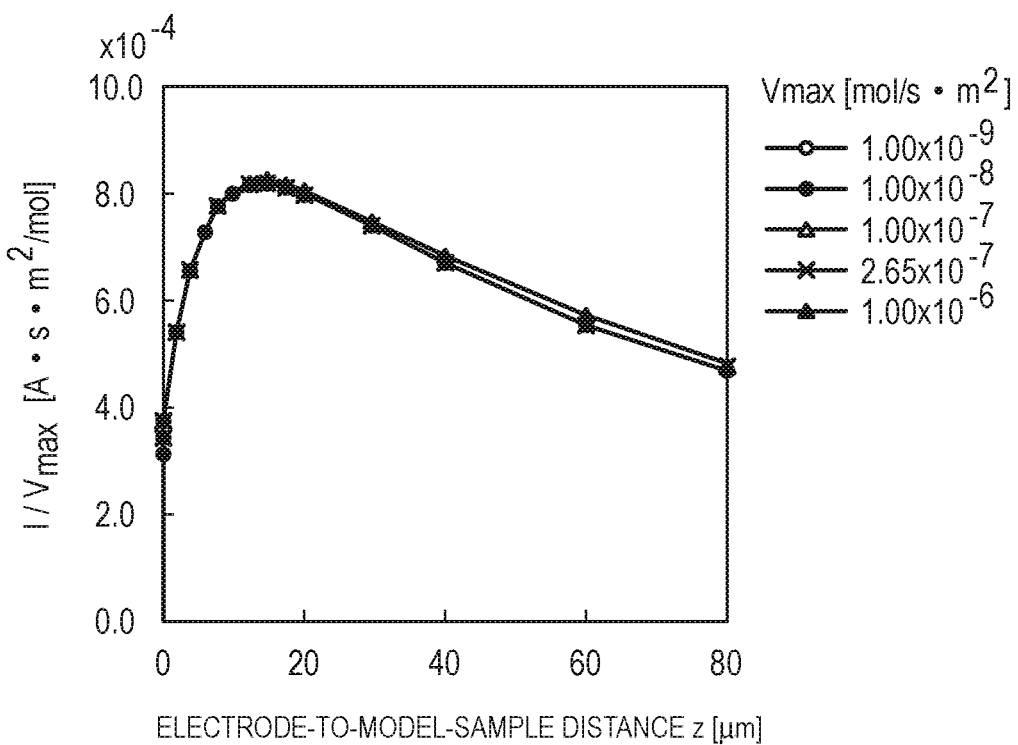
FIG. 4 is a graph showing a relationship between the electrode-to-sample distance z and the current value I/a rate $V_{max}$ of reaction.

It is clear from equation (1) that, if the substrate concentration [S] is sufficiently high, the rate v of generation is virtually determined by the rate $V_{max}$ of reaction when the substrate concentration is infinite. For this reason, the inventors investigated how the effective range for the distance z changed with the rate $V_{max}$ of reaction. FIG. 4 shows a result of simulating the current value I for each of various combinations of the rate $V_{max}$ of reaction and the distance z. The ordinate of the graph shown in FIG. 4 represents the current value I normalized with the rate $V_{max}$ of reaction. It is clear from FIG. 4 that a relationship between the current value I normalized with the rate $V_{max}$ of reaction and the distance z remains almost unchanged even if the rate $V_{max}$ of reaction changes and that the effective range for the distance z remains almost unchanged.

Figure 5:
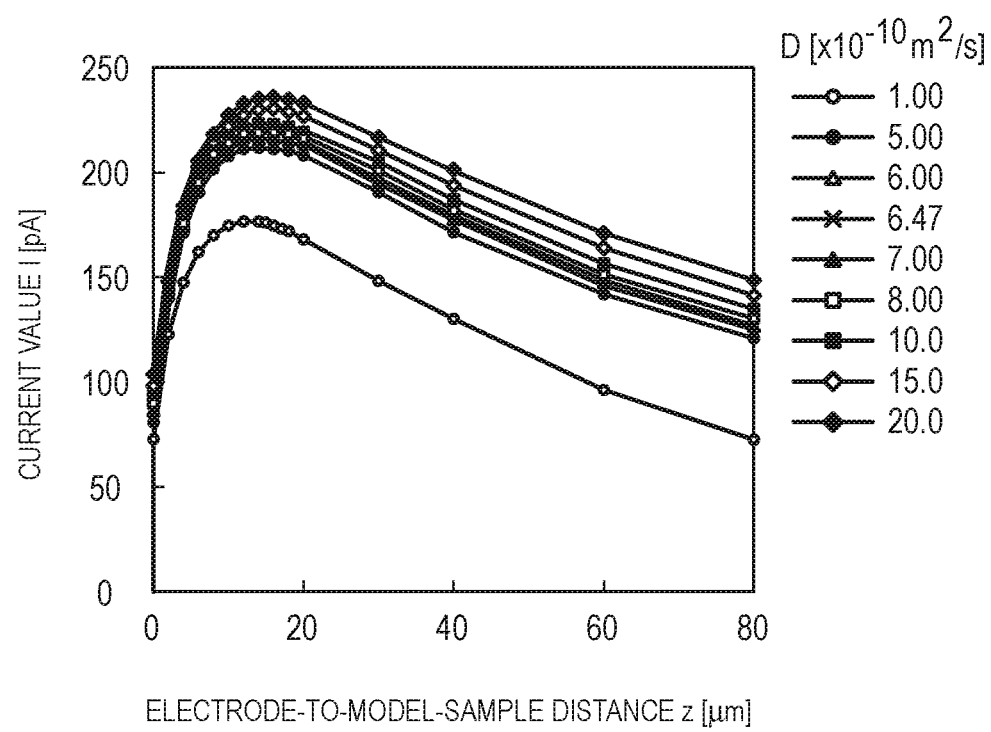
FIG. 5 is a graph showing a relationship among the electrode-to-sample distance z, the current value I, and a diffusion coefficient D.

Similarly, the inventors investigated how the effective range for the distance z changed with the diffusion coefficient D. FIG. 5 shows a result of simulating the current value I for each of various combinations of the diffusion coefficient D and the distance z. Values of the diffusion coefficient D for typical chemical substances to be detected used in the medical or life science field, such as PAP, iron complexes, ruthenium complexes, and hydrogen peroxide, range roughly from $1\times10^{-10}$ to $20\times10^{-10}$ m$^2$/s. It is clear from FIG. 5 that, if the diffusion coefficient D is within the range of $1\times10^{-10}$ to $20\times10^{-10}$ m$^2$/s, the relationship between the current value I and the distance z remains almost unchanged, and the effective range for the distance z remains almost unchanged.

As seen from the above-described results, equation (4) indicating a relationship between the distance z and the electrode diameter $d_{el}$ needed to achieve the above-described potent effects for biological samples having diameters of 100 to 600 μm is also useful for measurement systems having various values of the rate v of generation and various values of the diffusion coefficient D.

First Embodiment of Present Invention

Based on the simulation results described above, a first embodiment of an electrochemical measurement device according to the present invention has the configuration below. An electrochemical measurement device has a solution well 60, a spacer 10 or 50, a wall plate 31, and a plurality of working electrodes 21. The spacer 10 or 50, the wall plate 31, and the plurality of working electrodes 21 are all fixed on a flat surface 20a of the solution well 60. The flat surface 20a is a bottom surface of the solution well 60 which is in contact with a solution in a state where the solution well 60 contains the solution and is, for example, a surface of a semiconductor chip on which an integrated circuit is formed. A surface of each working electrode 21 which is in contact with the solution is an electrode surface 21a. The spacer 10 or 50, the electrode surfaces 21a, and the wall plate 31 are immersed in the solution during measurement.

<Biological Sample>

A biological sample 40 has a diameter not less than 100 μm and not more than 600 μm. The "diameter" of the biological sample 40 refers to the diameter of a smallest sphere which encompasses the biological sample 40.

<Spacer>

The spacer 10 or 50 has a profile surface at which a distance in a perpendicular direction to the flat surface 20a falls within a range for a distance z given by equation (4). The spacer 10 or 50 permits a dissolved substance in the solution to diffuse while inhibiting the biological sample 40 from entering a region on the flat surface 20a side of the profile surface.

In other words, the spacer 10 or 50 has a height of $h_1$ (a length from the flat surface 20a along a normal to the flat surface 20a) and a structure in which an enclosed three-dimensional region is not formed by the biological sample 40, the flat surface 20a, and the spacer 10 or 50 while the biological sample 40 is in contact with the spacer 10 or 50. $h_1$ is a predetermined value within the range for the distance z given by equation (4).

The biological sample 40 is arranged along the profile surface of the spacer 10 or 50. That is, the biological sample 40 is arranged in contact with the spacer 10 or 50.

With the above-described structure, the distance between the flat surface 20a and the biological sample 40 can be roughly kept at $h_1$. The "distance between the flat surface 20a and the biological sample 40" means a shortest distance between the flat surface 20a and the biological sample 40 and is a minimum length of a half line connecting an intersection of the normal to the flat surface 20a and the flat surface 20a and an intersection of the normal and the biological sample 40. The reason why the term "roughly" is used here is that the distance between the flat surface 20a and the biological sample 40 may be strictly less than $h_1$ depending on the shape and posture of the biological sample 40. Even in this case, the shapes of the individual biological samples 40 are strictly different from one another, and the postures of the individual biological samples 40 are strictly different from one another, so the above-described effect of "improving sensitivity, comparability, and reproducibility" is not lost from a statistical standpoint.

On the grounds that the distance between the flat surface 20a and the biological sample 40 may be strictly less than $h_1$, $h_1$ may be a predetermined value within a range for the distance z given by equation (4a). Equation (4a) means that an upper limit for the distance z is $21.8(d_{el}+0.8)/(d_{el}+9.7)+5$ [μm] and that a lower limit for z is $21.8(d_{el}+0.8)/(d_{el}+9.7)+0$ [μm]

$$z = \frac{21.8(d_{el} + 0.8)}{d_{el} + 9.7}(+5, 0)[\mu m] \qquad (4a)$$

$h_1$ may be a constant independent of a position on the flat surface 20a or a value determined by a function with the position on the flat surface 20a as a variable. Even in the latter case, $h_1$ is a value within the range for the distance z given by equation (4).

That is, the height 10 or 50 of the spacer 10 or 50 need not be uniform over a whole region on the flat surface 20a. For example, a region where the height of the spacer 10 or 50 is relatively low and a region where the height of the spacer 10 or 50 is relatively high may be present on the flat surface 20a. Alternatively, a region where the height of the spacer 10 or 50 changes in a stepwise manner may be present on the flat surface 20a.

<Electrode Surface>

Arrangement of an electrode surface is not particularly limited. For example, the distance between adjacent electrode surfaces is roughly not less than 120 μm. However, in actual usage, a distance L between a center of a first electrode surface corresponding to a first biological sample and a center of a second electrode surface corresponding to a second biological sample (the second biological sample is different from the first biological sample) needs to satisfy the condition that the first biological sample and the second biological sample are not contact each other while the first biological sample and the second biological sample are respectively arranged above the first electrode surface and the second electrode surface. That is, all electrode surfaces may be used or some electrode surfaces may be used in actual electrochemical measurement.

The electrode surface 21a of each working electrode 21 supplies or receives electrons to or from a chemical substance generated or consumed in the biological sample 40 having a diameter not less than 100 μm and not more than 600 μm. As a result, an oxidation-reduction reaction of the chemical substance progresses. All of the electrode surfaces 21a have diameters not more than 80 μm. Although the shape of each electrode surface 21a is preferably circular, the shape may be elliptical or polygonal. If the shape of the electrode surface 21a is non-circular, a diameter $d_{el}$ of the electrode surface 21a is $2[A/\pi]^{1/2}$. Note that A represents the area of the electrode surface 21a. A center of the electrode surface 21a is a geometrical center of the electrode surface 21a. If the shape of the electrode surface 21a is circular, the center of the electrode surface 21a is a center of a circle. If the shape of the electrode surface 21a is elliptical, the center of the electrode surface 21a is an intersection of a major axis and a minor axis of an ellipse. If the shape of the electrode surface 21a is rectangular, the center of the electrode surface 21a is an intersection of diagonal lines. If the electrode surface 21a has a complicated shape, a center of a minimum circle which encompasses the electrode surface 21a is defined as the center of the electrode surface 21a.

Although two electrode surfaces 21a are illustrated in FIGS. 6 to 12 to be referred to in the description below, the total number of electrode surfaces 21a is not limited to two. The arrangement shape of three or more electrode surfaces 21a is not limited. Any arrangement shape, such as a lattice shape (a shape with electrode surfaces located on lattice points), a linear shape (a shape with electrode surfaces located on a straight line), a circular shape (a shape with electrode surfaces located on a circle), or the shape of a polygonal frame (a shape with electrode surfaces located on sides of a polygon), can be selected.

<Wall Plate>

The wall plate 31 is placed between two electrode surfaces 21a adjacent to each other. The wall plate 31 has the property of being impervious to the dissolved substance in the solution. The wall plate 31 reduces crosstalk.

The shape of the wall plate 31 when the flat surface 20a is squarely viewed, that is, the shape of the wall plate 31 when the flat surface 20a is viewed from a normal direction of the flat surface 20a may be, for example, the shape of a straight line, the shape of a polygonal line, or a shape extending curvedly, or an annular shape or the shape of a polygonal frame. Note that, if the wall plate 31 has a closed structure as in the latter case, the wall plate 31 needs to be structured not to be in contact with the biological sample 40 while the biological sample 40 is in contact with the spacer 10 or 50.

The wall plate 31 has a height not less than the height of $h_1$. That is, the height of the wall plate 31 is above the range for the distance z represented by equation (4). There is no limit to an upper limit for the height of the wall plate 31. In actual usage, a solution surface exceeds the height of the wall plate 31 from the standpoint of uniformity of measurement conditions. Additionally, it is not required that the wall plate 31 is formed throughout the flat surface 20a. For example, the wall plate 31 is unnecessary in a location sufficiently away from the electrode surface 21a.

The relationship between the number of electrode surfaces and the number of wall plates is not particularly limited. However, it is unnecessary to uselessly form many wall plates. A configuration in which a plurality of electrode surfaces are arranged between adjacent wall plates or between a wall plate and a wall of the solution well is admissible.

<Type 1>

Figure 6A:
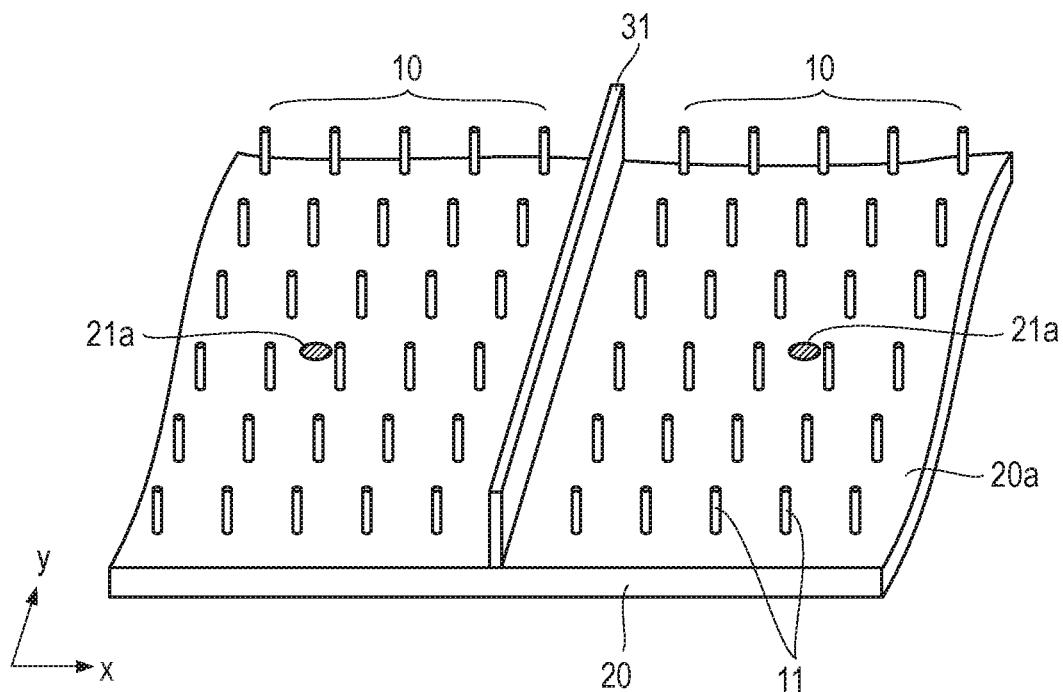
FIG. 6A is a schematic view for explaining a configuration of a main portion of a first embodiment (type 1) of an electrochemical measurement device according to the present invention.
Figure 6B:
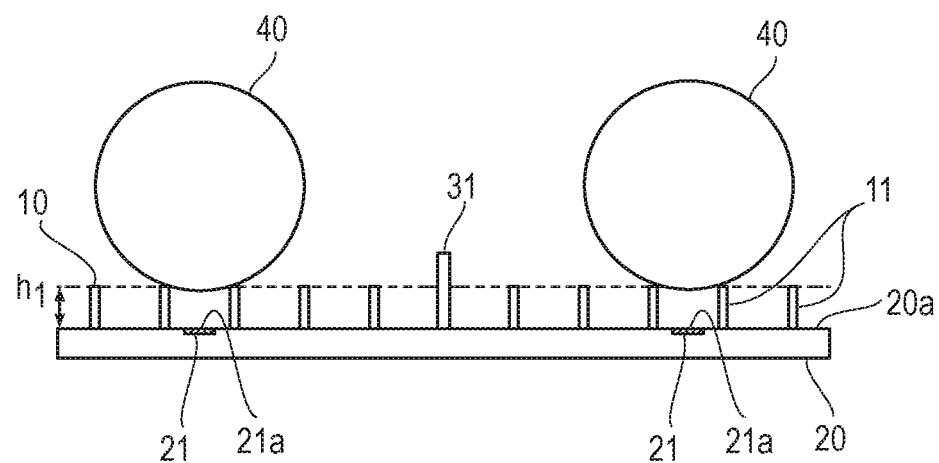
FIG. 6B is a schematic view for explaining the configuration of the main portion of the first embodiment (type 1) of the electrochemical measurement device according to the present invention.

FIGS. 6A and 6B show an example of the first embodiment of the electrochemical measurement device. The spacer 10 is composed of a plurality of pillar structures 11 standing close together. The wall plate 31 is placed between two adjacent electrode surfaces 21a. The pillar structures 11 having uniform heights extend from the flat surface 20a of a substrate 20, on which the electrode surfaces 21a are arranged, in the normal direction of the flat surface 20a. In this example, the interval between any two pillar structures 11 is less than 100 μm. For example, when the biological sample 40 having a diameter of 100 μm is to be measured, an electrochemical measurement device having the pillar structures 11 formed at intervals of about 30 μm is used. A broken line in FIG. 6B indicates a position of the profile surface that is away by a distance of $h_1$ from the flat surface 20a.

A supplemental explanation of the interval between the pillar structures 11 will be given. If the interval between the pillar structures 11 is set wide (for example, if the interval is slightly smaller than the diameter of the biological sample 40), although a path enough for the dissolved substance in the solution to diffuse can be secured, it is difficult to set the distance between the flat surface 20a and the biological sample 40 within the range for the distance z given by equation (4). On the other hand, if the interval between the pillar structures 11 is set narrow (for example, if the interval is significantly smaller than the diameter of the biological sample 40), although it is easy to set the distance between the flat surface 20a and the biological sample 40 within the range for the distance z given by equation (4), a path enough for the dissolved substance in the solution to diffuse cannot be secured, and it is difficult to keep the biological sample 40 at a position immediately above the electrode surface 21a. Thus, in actual usage, an electrochemical measurement device having a spacer composed of the pillar structures 11 that are appropriately arranged in accordance with the diameter and shape of the biological sample 40 is used. The intervals between the pillar structures 11 may not be fixed. Additionally, it is not required that the pillar structures 11 are formed throughout the flat surface 20a. For example, a spacer is unnecessary in a location sufficiently away from the electrode surface 21a.

The wall plate 31 extends in a straight line in a direction crossing a line segment connecting the centers of the two adjacent electrode surfaces 21a. In this example, the wall plate 31 extends in a y direction orthogonal to an array direction of the two electrode surfaces 21a standing side by side in an x direction. The wall plate 31 is placed at a position equally distant from the two adjacent electrode surfaces 21a. The wall plate 31 has a height not less than the heights of the pillar structures 11. That is, the height of the wall plate 31 is above the range for the distance z represented by equation (4).

The biological sample 40 is put above the electrode surface 21a by pipetting operation using a microscope, by using a guide, or the like. That is, a horizontal distance between the electrode surface 21a and the biological sample 40 (a distance in a direction parallel to the electrode surface 21a, that is, the flat surface 20a) is roughly 0. In this case, the distance z between the electrode surface 21a and the biological sample 40 falls roughly within the range in equation (4) even without performing a special operation. Thus, a path, through which the dissolved substance in the solution diffuses, is formed between the biological sample 40 and the electrode surface 21a. As a result, the amount of a chemical substance to be detected generated or consumed in the biological sample 40 increases. Additionally, since the volume of a three-dimensional region between the biological sample 40 and the electrode surface 21a increases, the amount of part of the generated or consumed chemical substance which stays inside the three-dimensional region increases. The two effects contribute to an increase in the amount of the chemical substance that reaches the electrode surface 21a.

With the presence of the spacer 10, a diffusion stroke between the biological sample 40 and the electrode surface 21a is long. The amount of the chemical substance that scatters away without reaching the electrode surface 21a is thus considered to increase. However, since the distance between the biological sample 40 and the electrode surface 21a is controlled by the spacer 10 so as to fall within an appropriate range, the two effects described earlier dominate, and, as a result, the amount of the chemical substance that reaches the electrode surface 21a is considered to increase.

<Type 2>

An "inverse-cone-shaped structure" in which the height of a spacer at a position closest to the center of the electrode surface 21a is lowest and increases gradually in a direction away from the center of the electrode surface 21a can be adopted as a spacer structure. If the biological sample 40 having a specific gravity higher than that of the solution is put in an electrochemical measurement device including the spacer 50 with this configuration by using a pipette or the like, the biological sample 40 can be sunk under its own weight toward a low position of the spacer 50, that is, the center of the electrode surface 21a without using any special mechanism. Thus, as for the positional relationship of the biological sample 40 with the electrode surface 21a, not only a distance in the normal direction of the flat surface 20a but also a distance in a direction parallel to the electrode surface 21a, that is, the flat surface 20a can be optimized.

Additionally, appropriate setting of the relationship between a horizontal distance (a distance in the direction parallel to the electrode surface 21a, that is, the flat surface 20a) m from a given point X on the flat surface 20a to the center of the electrode surface 21a and the height of the spacer at the point X allows the distance between the flat surface 20a and the biological sample to be set within the effective range for the distance z obtained by the above-described simulations as long as a biological sample diameter $d_{sp}$ has a value within the range of 100 to 600 µm.

Figure 7A:
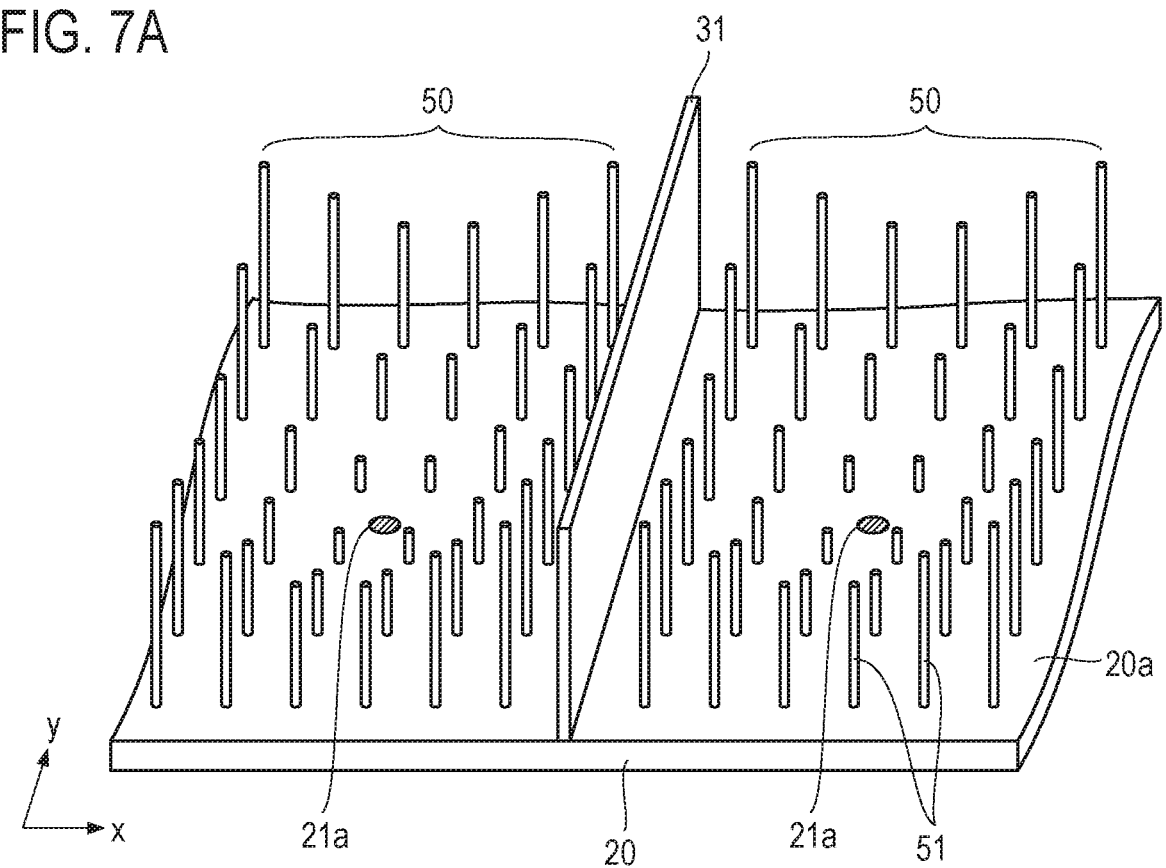
FIG. 7A is a schematic view for explaining a configuration of the main portion of the first embodiment (type 2) of the electrochemical measurement device according to the present invention.
Figure 7B:
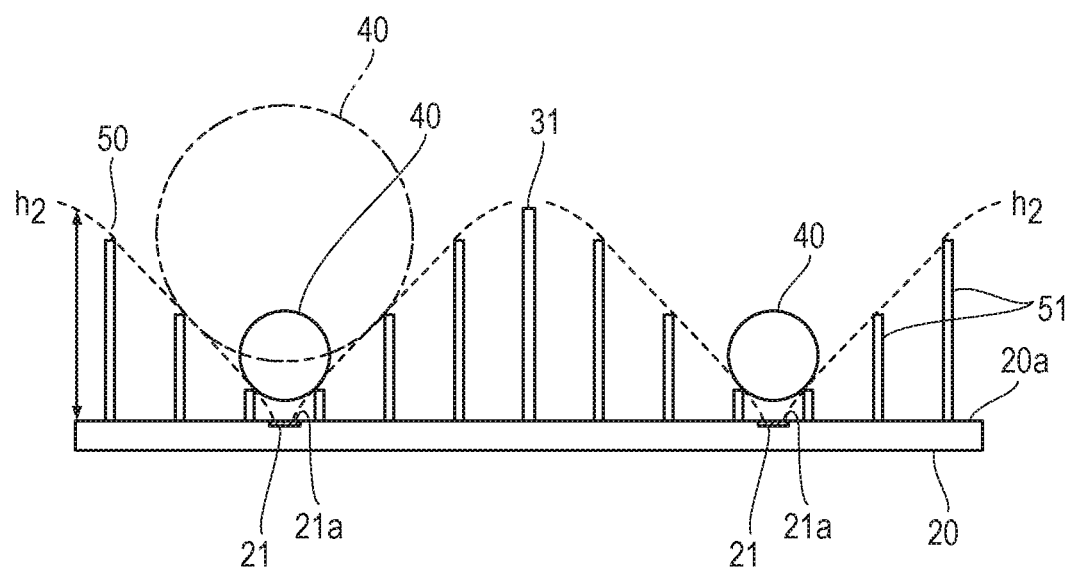
FIG. 7B is a schematic view for explaining the configuration of the main portion of the first embodiment (type 2) of the electrochemical measurement device according to the present invention.

FIGS. 7A and 7B illustrate an electrochemical measurement device including the spacer 50 having an inverse-cone-shaped structure. In FIGS. 7A and 7B, the spacer 50 having the inverse-cone-shaped structure is composed of a plurality of pillar structures 51 different in height. The pillar structures 51 standing close together extend from the flat surface 20a of the substrate 20, on which the electrode surfaces 21a are arranged, in the normal direction of the flat surface 20a. In this example, the interval between any two pillar structures 51 is less than 100 µm. For example, when the biological sample 40 having a diameter of 100 µm is to be measured, an electrochemical measurement device having the pillar structures 51 formed at intervals of about 30 µm is used. See the supplemental explanation on the interval between the pillar structures 11 for the interval between the pillar structures 51.

FIG. 7B illustrates two biological samples 40 different in diameter $d_{sp}$. If several values are appropriately selected as values of the diameter $d_{sp}$ from the range of 100 to 600 µm, and a curve circumscribing outlines of all of respective biological samples which are arranged at heights equal to optimum values of z for the values of $d_{sp}$, that is, $h_2$ indicated by a broken line in FIG. 7B is obtained by fitting, $h_2$ is roughly a median in equation (5) below. m represents a distance [unit: µm] from the center of the electrode surface 21a in the direction parallel to the flat surface 20a. Note that, letting L be a center-to-center distance between two adjacent electrode surfaces 21a which are closest, m at least satisfies $0 < m \leq L/2$ ($h_2 > 0$).

$$h_2 = \sqrt{(1.05d_{el} + 6.89)m} - 0.48d_{el} - 2.38 \pm 5 \ [\mu m] \tag{5}$$

The spacer 50 in this example has an inverse-cone-shaped profile surface in which the distance $h_2$ in the normal direction of the flat surface 20a that is dependent on the distance m [µm] satisfies equation (5). In a state where the biological sample 40 is in contact with the profile surface of the spacer 50 (that is, the pillar structures 51) in the solution and is located immediately above the center of the electrode surface 21a, electrochemical measurement is executed.

The wall plate 31 extends in a straight line in a direction crossing a line segment connecting centers of two adjacent electrode surfaces 21a. In this example, the wall plate 31 extends in the y direction orthogonal to an array direction of the two electrode surfaces 21a standing side by side in the x direction. The wall plate 31 is placed at a position equally distant from the two adjacent electrode surfaces 21a. The wall plate 31 has a height not less than a maximum height of the pillar structures 51. That is, the wall plate 31 has a height not less than a maximum value within a range for $h_2$ given by equation (5), where m is a horizontal distance of a point on the flat surface 20a located immediately below the wall plate 31 from the center of the electrode surface 21a closest to the point.

When the biological sample 40 is placed, the biological sample 40 can be sunk under its own weight toward a bottom portion of the inverse-cone-shaped spacer 50 without any special operation. At this time, a horizontal distance between the electrode surface 21a and the biological sample 40 (a distance in the direction parallel to the electrode surface 21a, that is, the flat surface 20a) is 0. Note that since a position where the biological sample 40 is in contact with the spacer 50 varies depending on the sample diameter $d_{sp}$, the distance z between the electrode surface 21a and a lower end of the biological sample 40 varies depending on $d_{sp}$.

As in the configuration shown in FIGS. 6A and 6B, a path, through which the dissolved substance in the solution diffuses, is formed between the biological sample 40 and the electrode surface 21a in the configuration shown in FIGS. 7A and 7B. Thus, the amount of a chemical substance to be detected generated or consumed in the biological sample 40 increases. Also, since the volume of a three-dimensional region between the biological sample 40 and the electrode surface 21a increases, the amount of part of the generated or consumed chemical substance which stays inside the three-dimensional region increases. The two effects contribute to an increase in the amount of the chemical substance that reaches the electrode surface 21a.

With the presence of the spacer 50, a diffusion stroke between the biological sample 40 and the electrode surface 21a is long. The amount of the chemical substance that scatters away without reaching the electrode surface 21a is thus considered to increase. However, since the distance between the biological sample 40 and the electrode surface 21a is controlled by the inverse-cone-shaped spacer 50 so as to fall within an appropriate range, the two effects described earlier dominate, and, as a result, the amount of the chemical substance that reaches the electrode surface 21a is considered to increase.

<Modification>

Although a spacer is composed of a plurality of pillar structures in the above-described examples, the present invention is not limited to this configuration. For example, a thin-plate porous structure having a large number of microscopic pores, such as an agarose gel, may be used as a spacer. The diameters of the microscopic pores may not be fixed. The porous structure is placed on the flat surface 20a. Additionally, it is not required that the spacer as the porous structure is formed throughout the flat surface 20a. For example, the spacer (porous structure) is unnecessary in a location sufficiently away from the electrode surface 21a.

Second Embodiment of Present Invention>

Based on the simulation results described above, a second embodiment of the electrochemical measurement device according to the present invention has the configuration below. An electrochemical measurement device includes a solution well 60, a plurality of wall plates 32 or 33, and a plurality of working electrodes 21. The plurality of wall plates 32 or 33 and the plurality of working electrodes 21 are all fixed on a flat surface 20a of the solution well 60. The flat surface 20a is a bottom surface of the solution well 60 which is in contact with a solution in a state where the solution well 60 contains the solution and is, for example, a surface of a semiconductor chip on which an integrated circuit is formed. A surface of each working electrode 21 which is in contact with the solution is an electrode surface 21a. The electrode surfaces 21a and the wall plates 32 or 33 are immersed in the solution during measurement.

<Biological Sample and Electrode Surface>

A biological sample 40 and the electrode surfaces 21a are the same as described in the above-described first embodiment.

<Wall Plate and Spacer>

Two or more wall plates 32 or 33 are placed between two electrode surfaces 21a adjacent to each other. The wall plates 32 or 33 have the property of being impervious to a dissolved substance in the solution. The wall plates 32 or 33 reduce crosstalk.

The wall plates 32 or 33 need to be shaped such that an enclosed three-dimensional region is not formed by the biological sample 40, the flat surface 20a, and the wall plates 32 or 33 while the biological sample 40 is in contact with the wall plates 32 or 33. For example, the shape of a straight line, the shape of a polygonal line, or a shape extending curvedly can be adopted as the shape of each wall plate 32 or 33 when the flat surface 20a is squarely viewed.

Alternatively, the wall plates 32 or 33 may be arranged at intervals in a cylindrical shape or the shape of a polygonal frame.

Alternatively, a structure in a cylindrical shape or the shape of a polygonal frame having one or more slits formed therein can be adopted as the wall plate 32 or 33.

The interval between the wall plates 32 or 33 may not be fixed. Additionally, it is not required that the wall plates 32 or 33 are formed throughout the flat surface 20a. For example, the wall plate 32 or 33 is unnecessary in a location sufficiently away from the electrode surface 21a.

A height of $h_1$ (a length from the flat surface 20a along a normal to the flat surface 20a) of each wall plate 32 or 33 has a predetermined value within a range for a distance z given by equation (4).

In the second embodiment, the plurality of wall plates 32 or 33 have a function as a spacer. A spacer composed of the plurality of wall plates 32 or 33 has a profile surface at which a distance in a perpendicular direction to the flat surface 20a falls within the range for the distance z given by equation (4). The spacer permits the dissolved substance in the solution to diffuse while inhibiting the biological sample 40 from entering a region on the flat surface 20a side of the profile surface.

With the above-described structure, the distance between the flat surface 20a and the biological sample 40 can be roughly kept at $h_1$. The "distance between the flat surface 20a and the biological sample 40" means a shortest distance between the flat surface 20a and the biological sample 40 and is a minimum length of a half line connecting an intersection of the normal to the flat surface 20a and the flat surface 20a and an intersection of the normal and the biological sample 40. The reason why the term "roughly" is used here is that the distance between the flat surface 20a and the biological sample 40 may be strictly less than $h_1$ depending on the shape and posture of the biological sample 40. Even in this case, the shapes of the individual biological samples 40 are strictly different from one another, and the postures of the individual biological samples 40 are strictly different from one another, so the above-described effect of "improving sensitivity, comparability, and reproducibility" is not lost from a statistical standpoint.

On the grounds that the distance between the flat surface 20a and the biological sample 40 may be strictly less than $h_1$, $h_1$ may be a predetermined value within a range for the distance z given by equation (4a).

$h_1$ may be a constant independent of a position on the flat surface 20a or a value determined by a function with the position on the flat surface 20a as a variable. Even in the latter case, $h_1$ is a value within the range for the distance z given by equation (4).

That is, the height of the wall plate 32 or 33 need not be uniform over a whole region on the flat surface 20a. For example, a region where the height of the wall plate 32 or 33 is relatively low and a region where the height of the wall plate 32 or 33 is relatively high may be present on the flat surface 20a. Alternatively, a region where the heights of the wall plates 32 or 33 change in a stepwise manner may be present on the flat surface 20a.

<Type 1>

Figure 8A:
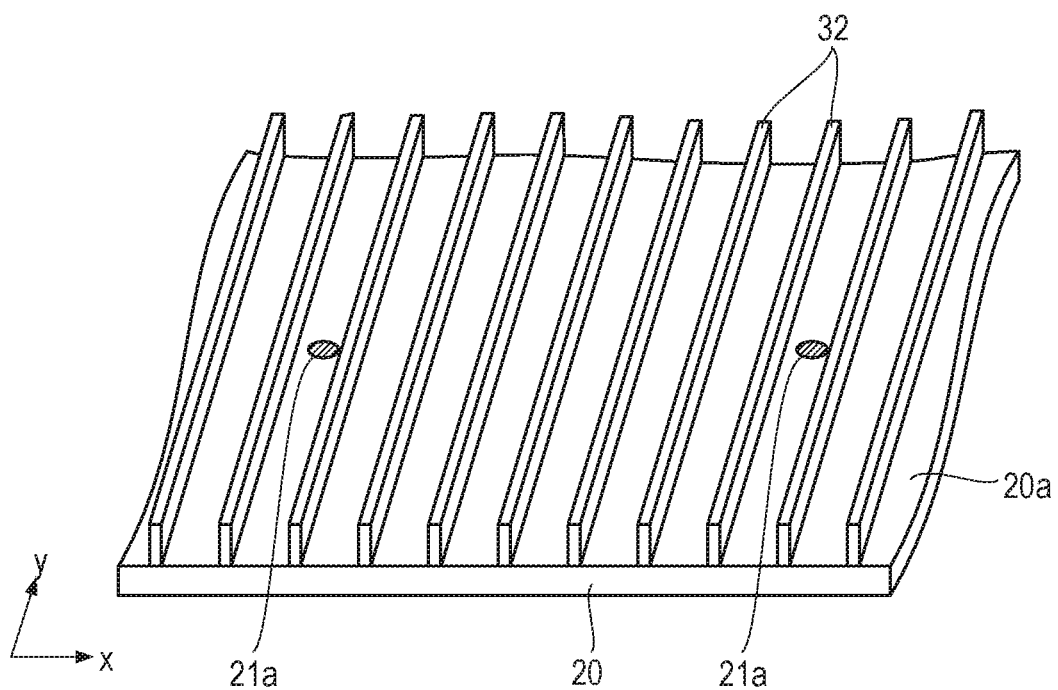
FIG. 8A is a schematic view for explaining a configuration of a main portion of a second embodiment (type 1) of the electrochemical measurement device according to the present invention.
Figure 8B:
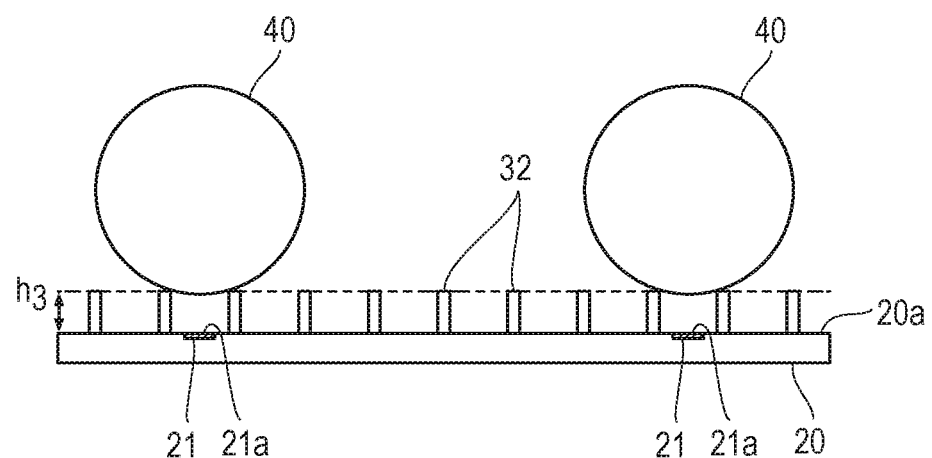
FIG. 8B is a schematic view for explaining the configuration of the main portion of the second embodiment (type 1) of the electrochemical measurement device according to the present invention.

In an example shown in FIGS. 8A and 8B, two or more wall plates 32 are arrayed on the flat surface 20a in an x direction at intervals less than 100 μm. The wall plates 32 extend in a straight line in a y direction. Two electrode surfaces 21a are arranged in the x direction on the flat surface 20a of a substrate 20, on which an x-y orthogonal coordinate system is defined.

For the same reason as that in the case of a pillar structure, in actual usage, an electrochemical measurement device having a spacer composed of the wall plates 32 that are appropriately arranged in accordance with the diameter and shape of the biological sample 40 is used.

In the example in FIGS. 8A and 8B, the plurality of wall plates 32 have uniform heights. A height $h_3$ of each wall plate 32 falls within the range for z given by equation (4). That is, the height $h_3$ satisfies the equation below.

$$h_3 = \frac{21.8(d_{el} + 0.8)}{d_{el} + 9.7} \pm 5[\mu m]$$

In the configuration shown in FIGS. 8A and 8B, the plurality of wall plates 32 have the same function as that of the plurality of pillar structures 11 shown in FIGS. 6A and 6B, that is, a function as a spacer and further have the same function as that of the wall plate 31 shown in FIGS. 6A and 6B, that is, a function as a wall plate which reduces crosstalk.

Note that although y coordinates of centers of the two electrode surfaces 21a match up with each other in the example in FIGS. 8A and 8B, the y coordinates of the centers of the two electrode surfaces 21a need not match up with each other. That is, a line connecting the centers of the two electrode surfaces 21a and an extension direction of the wall plates 32 may not be orthogonal to each other. In other words, the angle which the line connecting the centers of the two electrode surfaces 21a forms with the extension direction of the wall plates 32 may be larger than 0 degrees and smaller than 90 degrees.

<Type 2>

Figure 9A:
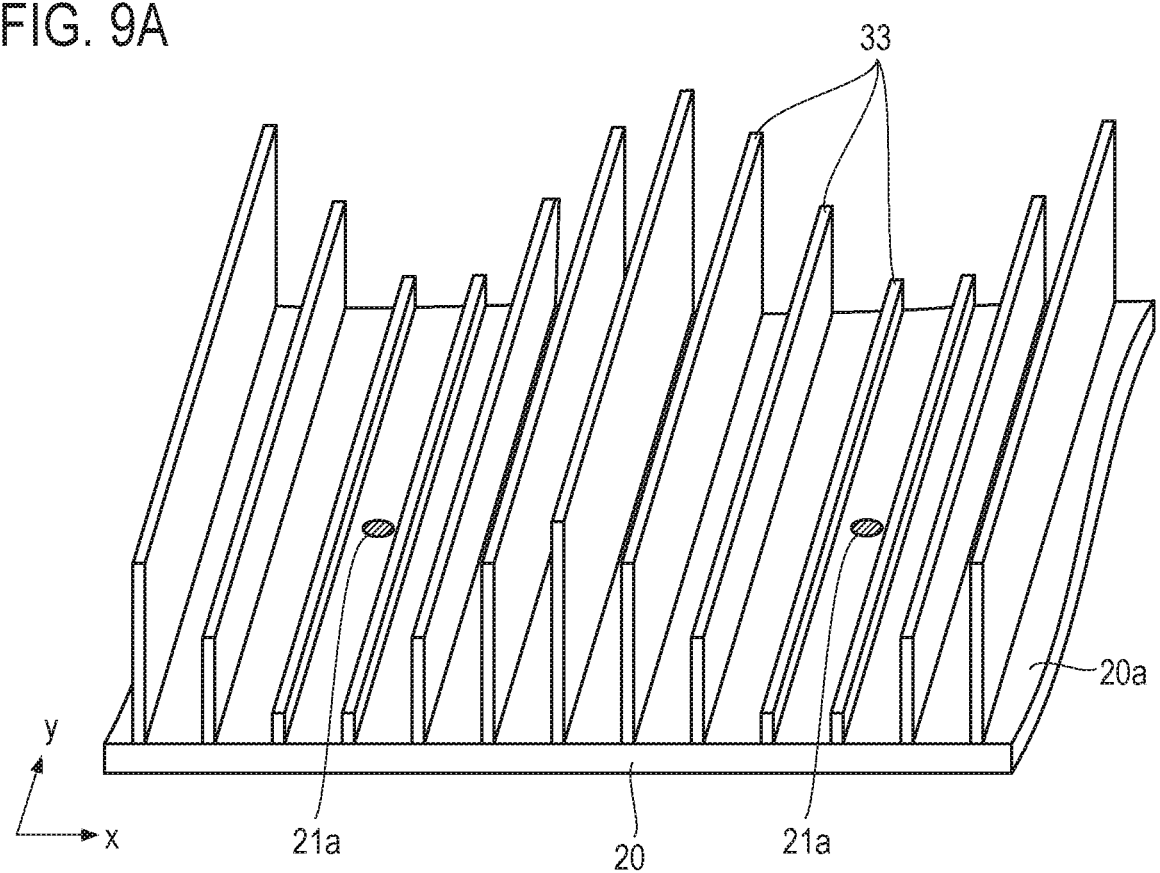
FIG. 9A is a schematic view for explaining a configuration of the main portion of the second embodiment (type 2) of the electrochemical measurement device according to the present invention.
Figure 9B:
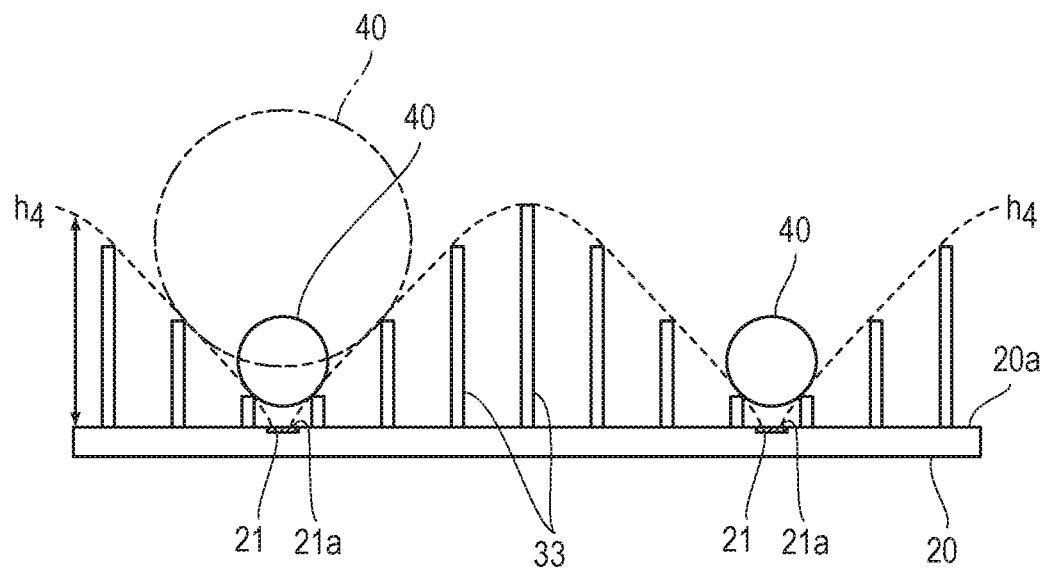
FIG. 9B is a schematic view for explaining the configuration of the main portion of the second embodiment (type 2) of the electrochemical measurement device according to the present invention.

In a configuration shown in FIGS. 9A and 9B, the plurality of wall plates 33 have the same function as that of the plurality of pillar structures 51 shown in FIGS. 7A and 7B, that is, a function as a spacer and further have the same function as that of the wall plate 31 shown in FIGS. 7A and 7B, that is, a function as a wall plate which reduces crosstalk.

The plurality of wall plates 33 are arrayed on the flat surface 20a in the x direction at intervals less than 100 μm. The wall plates 33 extend in a straight line in the y direction. See the description of the interval between the wall plates 32 for the interval between the wall plates 33. A height $h_4$ of the wall plate 33 at a position away by a distance m from the center of the electrode surface 21a in the x direction satisfies equation (5). That is, $h_4 = h_2$. In this example, the heights of the wall plates 33 do not change in the y direction.

A cross-section taken perpendicularly to a y-axis of the wall plates 33 has a parabolic cross-sectional shape. A profile surface of the wall plates 33 is a groove-like surface which extends in the y direction. One or more electrode surfaces 21a are arranged along a groove (a bottom of an inverse cone).

In the example in FIGS. 9A and 9B, y coordinates of centers of the two electrode surfaces 21a match up with each other. The y coordinates of the centers of the two electrode surfaces 21a, however, need not match up with each other. That is, a line connecting the centers of the two electrode surfaces 21a and an extension direction of the wall plates 33 may not be orthogonal to each other. In other words, the angle which the line connecting the centers of the two electrode surfaces 21a forms with the extension direction of the wall plates 33 may be larger than 0 degrees and smaller than 90 degrees. Electrode rows preferably form an array in which the electrode surfaces 21a are also arranged in the x direction. There is no limit to arrangement (y coordinates) of the electrode surfaces 21a in an electrode row. A configuration in which one electrode row includes only one electrode surface 21a is also admissible.

The wall plates 32 and 33 in FIGS. 8A and 8B and FIGS. 9A and 9B have the property of being impervious to the dissolved substance in the solution. The wall plates 32 and 33 reduce crosstalk.

<Modifications>

Figure 10:
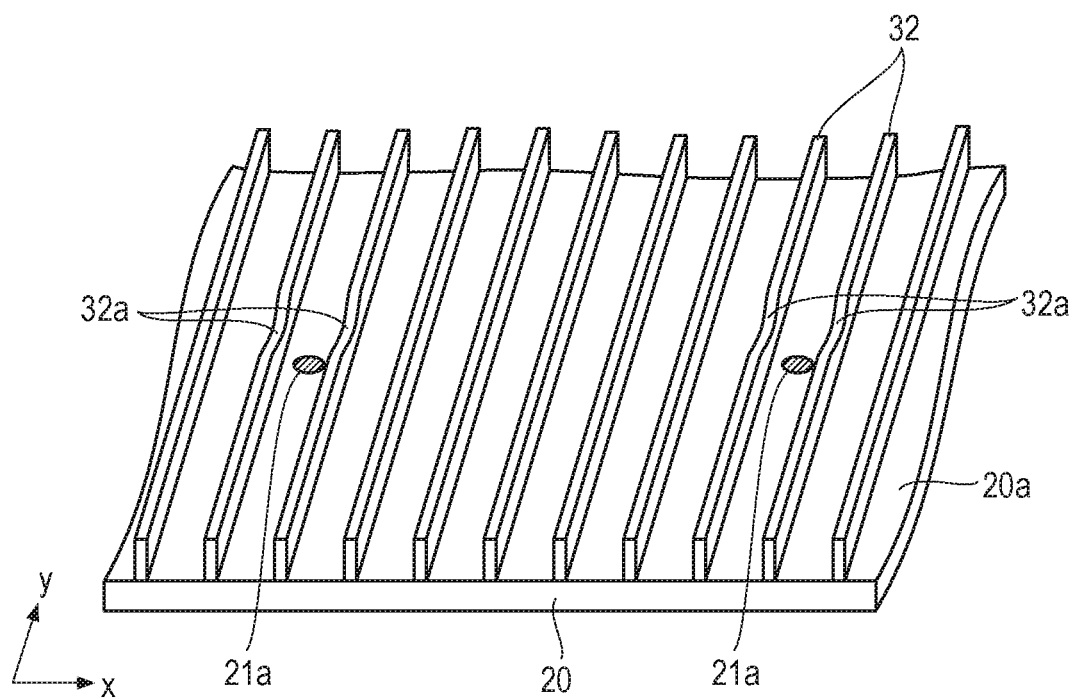
FIG. 10 is a schematic view for explaining a configuration of a main portion of a modification of the second embodiment of the electrochemical measurement device according to the present invention.
Figure 11:
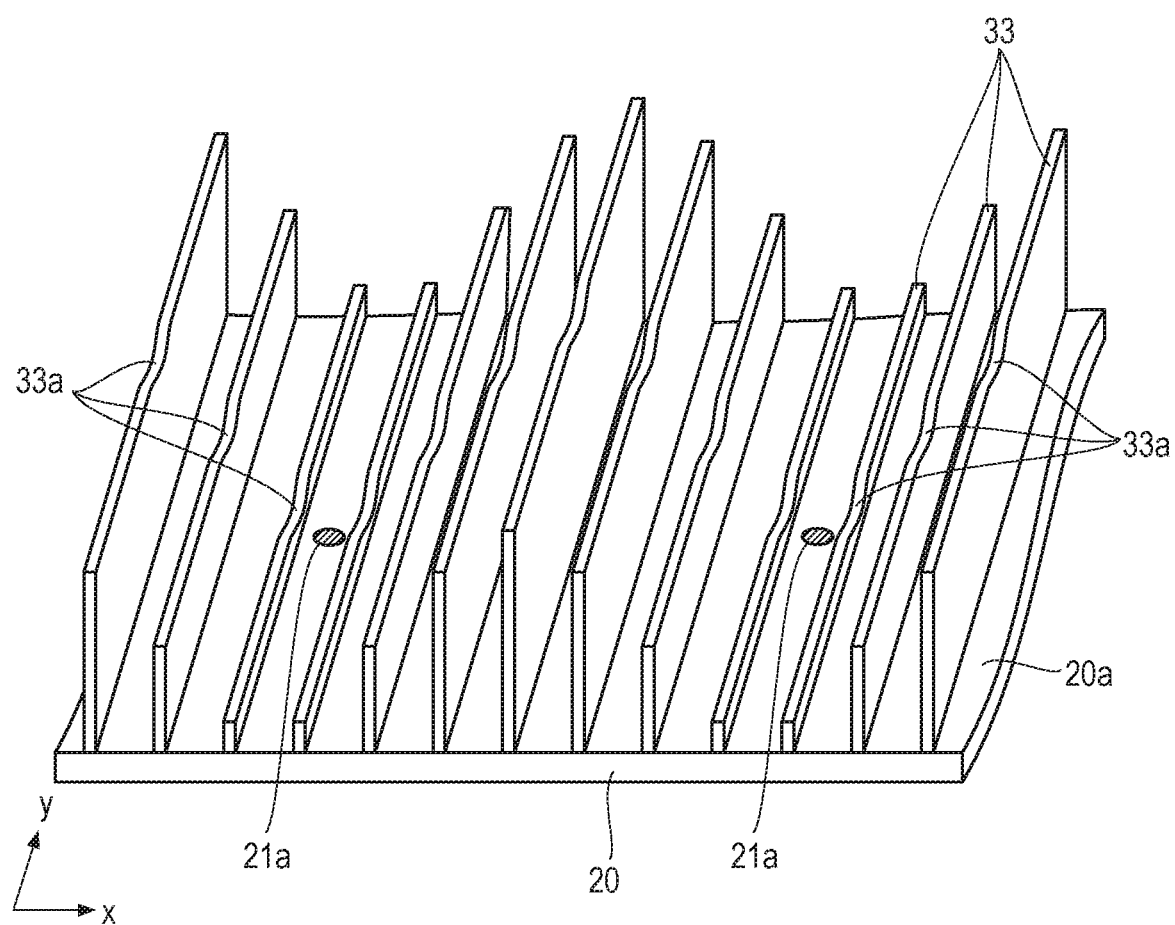
FIG. 11 is a schematic view for explaining a configuration of a main portion of a modification of the second embodiment of the electrochemical measurement device according to the present invention.

FIGS. 10 and 11 show modifications of the configurations shown in FIGS. 8A and 8B and FIGS. 9A and 9B. In the modifications, each wall plate extends continuously in a straight line.

Two wall plates 32 located next to each electrode surface 21a of the wall plates 32 shown in FIG. 10 have heights which change along a y direction (an extension direction of the wall plates 32). In this example, changes in the heights are noticeable near the electrode surface 21a, and there are no changes in the heights except near the electrode surface 21a. The height of each wall plate 32 is lowest (minimal) at a point where a perpendicular line from a center of the electrode surface 21a to the wall plate 32 crosses the wall plate 32 when the flat surface 20a is squarely viewed. Although the height of the wall plate 32 changes smoothly in the example shown in FIG. 10, the height may change in a stepwise manner. In the example shown in FIG. 10, a minimum value of the height in one of the two wall plates 32 located next to the electrode surface 21a is almost equal to a minimum value of the height in the other.

In other words, depressions 32a are formed at respective upper portions of the two wall plates 32 located next to the electrode surface 21a. Each depression 32a is located above the point where a perpendicular line from the center of the electrode surface 21a to the wall plate 32 crosses the wall plate 32 when the flat surface 20a is squarely viewed.

In the above-described example, the height of the wall plate 32 at a position where the spherical biological sample 40 is in contact with the wall plate 32 while the biological sample 40 is put in the depression 32a is equal to $h_3$ described above.

Similarly, the height of each wall plate 33 shown in FIG. 11 changes along a y direction (an extension direction of the wall plates 33). In this example, a change in the height of each wall plate 33 is noticeable near the electrode surface 21a, and there is no change in the height except near the electrode surface 21a. The height of each wall plate 33 is lowest (minimal) at the point where a perpendicular line from a center of the electrode surface 21a to the wall plate 33 away by a distance m crosses the wall plate 33 when the flat surface 20a is squarely viewed. Although the height of the wall plate 33 changes smoothly in the example shown in FIG. 11, the height may change in a stepwise manner. In the example shown in FIG. 11, a minimum value of the height in one of two wall plates 32 which are located at positions symmetric with respect to the center of the electrode surface 21a is almost equal to a minimum value of the height in the other.

In other words, a depression 33a is formed at an upper portion of each wall plate 33. Each depression 33a is located above the point where a perpendicular line from the center of the electrode surface 21a to the wall plate 33 crosses the wall plate 33 when the flat surface 20a is squarely viewed.

In the above-described example, the height of the wall plate 33 at a position where the spherical biological sample 40 is in contact with the wall plate 33 away by the distance m from the center of the electrode surface 21a while the biological sample 40 is put in the depression 33a is equal to $h_4$ described above.

The depressions 32a and 33a are useful for positioning of a biological sample in the y direction.

The depressions 32a are provided at one pair of wall plates 32, which is adjacent to the electrode surface 21a and between which the electrode surface 21a is sandwiched, in FIG. 10 while the depressions 33a are provided at all the wall plates 33 in FIG. 11. The amounts of depression of the depressions 32a and 33a are set within ranges where the heights $h_3$ and $h_4$ are achieved.

In modifications as well, in which depressions are formed at wall plates, y coordinates of centers of two electrode surfaces 21a need not match up with each other, as in the example in FIGS. 8A and 8B. Alternatively, the depression 32a may be formed only at the wall plate 32 closest or second closest to a center of each electrode surface 21a (either one if two wall plates 32 are present at positions equally distant from the center of the electrode surface 21a). If the wall plate 32 is located above the electrode surface 21a, the depression 32a is located above the electrode surface 21a. The depression 32a may be formed at an upper portion of each of three or more wall plates 32 near the electrode surface 21a.

In the example shown in FIG. 11, letting L be a center-to-center distance between two adjacent electrode surfaces 21a which are closest, the depression 33a is formed at an upper portion of the wall plate 33 at a position away by the distance m from a center of the electrode surface 21a, where m satisfies 0<m≤L/2. However, since a maximum diameter of the biological sample 40 is 600 µm, a structure in which the depression 33a is formed at an upper portion of the wall plate 33 away by the distance m, not less than 0 and not more than 300 µm, from the center of the electrode surface 21a may be adopted.

That is, the depression 33a is formed at all of the wall plates 33, widths of which are wholly included in a line segment connecting a first end point and a second end point located on two sides of each electrode surface. Note that the line segment connecting the first end point and the second end point is parallel to the x direction. The first end point and the second end point are each a closer one of a point 300 µm away from a center of the electrode surface and a midpoint of the adjacent electrode rows. Note that, if the former point and the latter point match up with each other, the first end point or the second end point is at the matching points.

FIG. 11 represents a form in a case where x-direction distances from two electrode rows illustrated (the electrode surfaces 21a) to a midpoint of the two electrode rows are less than 300 µm and no other electrode row is present outside the two electrode rows illustrated (the electrode surfaces 21a) in the above-described configuration. Note that since a width of the highest wall plate 33 that is located right on the midpoint of the two electrode surfaces 21a does not fall wholly within ranges for the left and right electrode rows, each having the first and second end points as two ends, the depression 33a may not be formed at the wall plate 33 or may be formed as in the illustrated example.

Alternatively, the depression 33a may be formed at at least one wall plate 33 among the wall plates 33, widths of which fall at least partly within an x-direction range between first and second end points, instead of providing the depressions 33a at all of the wall plates 33 falling within the range between the first and second end points.

With a depression formed at an upper portion of a wall plate, a biological sample can be positioned in the y direction. That is, the biological sample 40 can be located almost immediately above each electrode surface 21a. If the wall plate 33 is located above the electrode surface 21a, the depression 33a is located above the electrode surface 21a.

Figure 12:
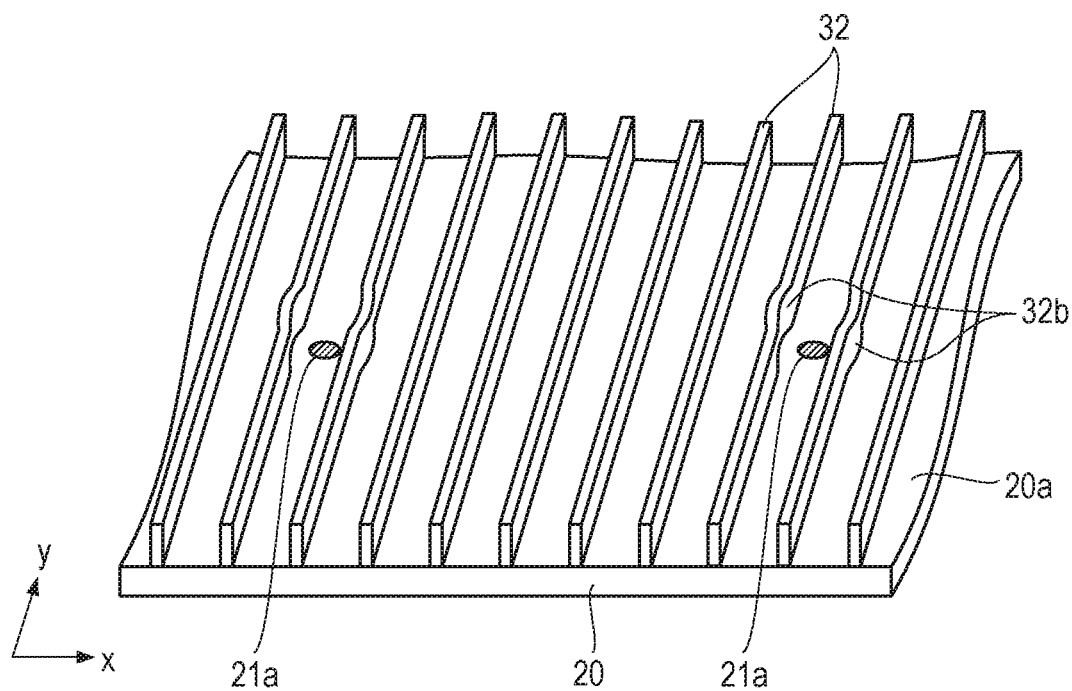
FIG. 12 is a schematic view for explaining a configuration of a main portion of a modification of the second embodiment of the electrochemical measurement device according to the present invention.

FIG. 12 shows another modification of the configuration shown in FIGS. 8A and 8B. In the modification, each wall plate 32 extends continuously.

The interval between two wall plates 32 located next to each electrode surface 21a of the wall plates 32 shown in FIG. 12 changes along a y direction (an extension direction of the wall plates 32). In this example, a change in interval is noticeable near the electrode surface 21a, and there is no change in interval except near the electrode surface 21a. For this reason, an extension direction of portions without a change in interval (that is, portions except near the electrode surface 21a) is regarded as an extension direction of a wall plate. The interval between the wall plates 32 is widest (maximal) at a point where a line extending from a center of the electrode surface 21a and orthogonal to the extension direction of the wall plates 32 crosses the wall plate 32 when the flat surface 20a is squarely viewed. Although the interval between the wall plates 32 changes smoothly in the example shown in FIG. 12, the interval may change in a stepwise manner.

In other words, a recess 32b which extends in a wall-plate height direction (that is, a normal direction of the flat surface 20a) is formed at each of the two wall plates 32 located next to the electrode surface 21a. The recess 32b has a portion which opens toward the center of the electrode surface 21a when the flat surface 20a is squarely viewed.

With widening of a wall plate interval, a biological sample can be positioned.

In the example in FIG. 12, y coordinates of centers of the two electrode surfaces 21a match up with each other. However, the y coordinates of the centers of the two electrode surfaces 21a need not match up with each other. That is, a line connecting the centers of the two electrode surfaces 21a may not be orthogonal to the extension direction of the wall plates 32. In other words, the angle which the line connecting the centers of the two electrode surfaces 21a forms with the extension direction of the wall plates 32 may be larger than 0 degrees and smaller than 90 degrees.

Unlike the example in FIG. 12, the recess 32b may be formed only at one wall plate. The one wall plate in this case may be a wall plate second closest to the center of the electrode surface 21a.

The shape of each recess when the flat surface 20a is squarely viewed may be the shape of a polygonal line or the shape of a curved line.

Figure 13:
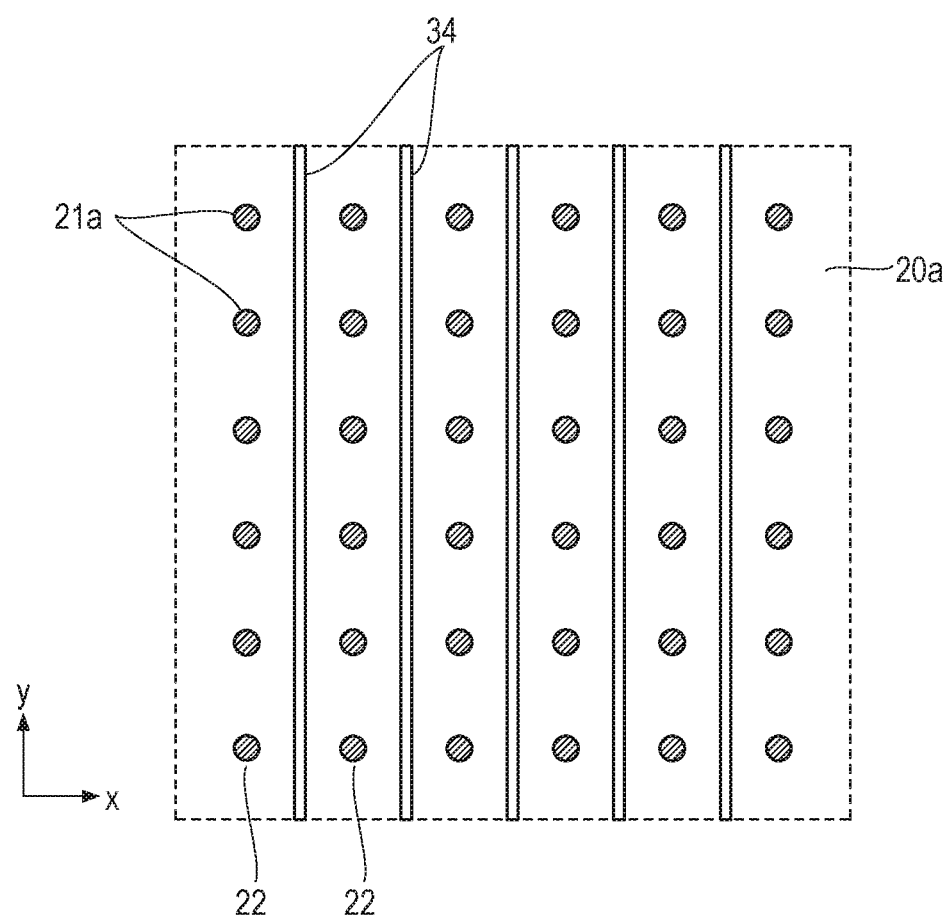
FIG. 13 is a view for explaining an example of arrangement of wall plates with respect to electrode surfaces arrayed in an array.

FIG. 13 shows an example in which the electrode surfaces 21a are arrayed in a lattice pattern. A plurality of electrode rows 22 are arranged in an x direction, thereby arraying a large number of electrode surfaces 21a. In each electrode row 22, a plurality of electrode surfaces 21a are arranged in a y direction. In this configuration, wall plates 34 which reduce crosstalk, for example, each extend in the y direction between adjacent ones of the electrode rows 22. In this case, the effect of reducing crosstalk in the x direction is achieved. Even if the wall plates 34 are placed in this manner, a dissolved substance is not blocked from diffusing in a direction parallel to the wall plates 34 (the y direction), a reduction in the amount of the dissolved substance supplied is small. A spacer is not shown in FIG. 13.

In the configuration shown in FIG. 13, the spacer not shown is the pillar structures 11 or 51 shown in FIGS. 6A and 6B or FIGS. 7A and 7B, a porous structure, or the like.

In the configuration shown in FIG. 13, the spacer not shown may be the plurality of wall plates 32 or 33 shown in one of FIGS. 8 to 12 that have a function as a spacer. In other words, in an electrochemical measurement device having the configuration shown in one of FIGS. 8 to 12, the wall plate 34 (a partition plate) having a height above the heights of the wall plates 32 and 33 may be additionally placed. The height of the wall plate 34 may be above a range for the height $h_3$ or $h_4$ of the wall plate 32 or 33. If the height of the wall plate 34 is sufficiently high, most of the effect of reducing crosstalk is achieved by the wall plate 34. If a spacer is composed of a plurality of wall plates, a breakproof, robust electrochemical measurement device can be implemented.

<Specific Example>

The above-described effects are expected to be achieved as long as the condition that "a chemical substance generated or consumed in a biological sample itself is electrochemically active or is transformed to another chemical substance that is electrochemically active" is satisfied. The type of a biological sample, a reaction mechanism by which a chemical substance to be detected is generated or consumed in the biological sample, a working electrode, a substrate on which the working electrode is formed, and the like are not particularly limited. For example, the configurations below are conceivable.

<Biological Sample>

An embryoid body which was produced from mouse ES cells was selected as a biological sample for the simulations. However, the biological sample may be a cell aggregate, a single cell, a piece of tissue, a microorganism, a non-biological sample containing a biologically-relevant substance, or the like.

<Reaction Mechanism by Which Chemical Substance is Generated or Consumed in Biological Sample>

An ALP enzymatic reaction on a model sample was selected as a reaction mechanism for the simulations. However, the reaction mechanism may be an enzymatic reaction of protein, peptide, RNA, or the like or a catalytic reaction with a platinum thin film, a titanium oxide thin film, or the like on a biological sample.

If a biological sample is cells or the like, a chemical substance may be a substance generated or consumed through various metabolic pathways or signaling pathways in cells. For example, the chemical substance may be protons released in a metabolic pathway in a glycolytic system or dopamine released from neuron cells.

<Working Electrode>

The material for a working electrode was not specified in the simulations. Any material, such as a noble metal (for example, gold or platinum), an inorganic substance predominantly composed of carbon (for example, graphite, diamond doped with an impurity, or a carbon nanotube), or a conductive polymer (for example, polypyrrole, polyaniline, or polythiophene), may be used as the material for the working electrode as long as the material can be used for a working electrode for electrochemical measurement.

The shape of an electrode surface of the working electrode is, for example, circular, elliptical, polygonal, or the like.

<Substrate>

The material for a substrate was not specified in the simulations. Any material, such as quartz, glass, silicon, or ceramic, may be used as the material for the substrate as long as the material can be used for a working electrode support for electrochemical measurement.

<Specific Example of Spacer Fabrication Method>

In order to achieve the above-described effects, a spacer is desirably fabricated by a method capable of controlling the height of the spacer on the order of μm. The spacer has a solution-permeable structure, that is, a structure which permits a dissolved substance in a solution to diffuse. Additionally, if the spacer is to come into contact with an electrode, the spacer needs to have electrical insulation. As long as these conditions are satisfied, there is no limit to a fabrication method for the spacer and the material for the spacer. Preferable spacer fabrication methods and preferable materials for the spacer will be illustrated below.

<Fabrication Example 1 of Spacer Composed of Plurality of Pillar Structures>

1) A silicon nitride film is formed on a substrate by chemical vapor deposition (CVD). The thickness of the silicon nitride film on the substrate is uniform.

2) An etching protective layer is patterned on the silicon nitride film by photolithography.

3) The silicon nitride film in a region not coated with the etching protective layer is etched by reactive ion etching, thereby forming pillar structures.

4) The etching protective layer is removed.

The material for the insulating film (the material for the pillar structures) is not limited to silicon nitride and may be, for example, silicon oxide, titanium oxide, or the like.

The film formation method is not limited to CVD and may be a vacuum film formation method, such as sputtering or evaporation, spin-on glass, or the like.

The patterning method for the etching protective layer is not limited to photolithography and may be screen printing, ink-jet printing, or the like.

The etching method is not limited to reactive ion etching and may be plasma etching, sputter etching, ion beam etching, or wet etching.

<Fabrication Example 2 of Spacer Composed of Plurality of Pillar Structures>

1) An LSI having a current sensing element is coated with photosensitive resin by spin coating. The current sensing element includes at least a working electrode.

2) Pillar structures are fabricated by photolithography.

The photosensitive resin may be any insulating and photosensitive resin as long as the resin is used in common photolithography. A photosensitive resin necessary for achievement of resolution required to fabricate a spacer having an accurate diameter and an accurate height is desirably selected. An epoxy chemically-amplified photosensitive resin which is used as a negative permanent resist is preferable from the standpoint of the chemical stability of the pillar structures.

Any coating method may be used as long as the coating method can control a film thickness on the order of µm. In view of high film-thickness controllability, the coating method is not limited to spin coating and may be spray coating, dip coating, screen coating, roll coating, or the like.

<Fabrication Example of Spacer as Porous Structure>

1) After an agarose solution diluted with water is prepared, the agarose solution diluted with water is heated to 80° C. or more and is changed to a sol.

2) The agarose aqueous solution is dropped onto a substrate at 80° C., and a thin film is formed by spin coating. During the process, the temperature of the substrate is constantly kept at 80° C. or more.

3) The substrate is left and cooled to the room temperature to acquire a porous spacer made of agarose gel.

Any sol may be used as the sol to be dropped onto the substrate as long as the sol changes to a porous gel after coating. The heating temperature is appropriately set depending on the type of the sol. In view of ease of preparation and high biocompatibility, agarose, polyvinyl alcohol, cellulose, or the like is preferable.

Any method may be used as the coating method as long as the method can control a film thickness on the order of µm and has a mechanism for keeping the temperature of the sol constant during the coating process. In view of high film-thickness controllability, the coating method is not limited to spin coating and may be spray coating, dip coating, screen coating, roll coating, or the like.

<Others>

A spacer composed of pillar structures can be fabricated by molding (nanoimprinting (nanoimprint lithography) or insert molding), printing (for example, screen printing or ink-jet printing), machining, or the like.

A spacer which is a porous structure can also be fabricated by placing a pre-shaped porous body, such as porous silica or a nitrocellulose membrane, on a substrate.

<Specific Example of Wall Plate Fabrication Method>

If wall plates have a function as a spacer as in the examples shown in FIGS. 8 and 9, the wall plates are desirably fabricated by a method capable of controlling a wall plate height on the order of µm. If a wall plate is fabricated in contact with an electrode, the wall plate needs to have electrical insulation. In these respects, the same method as a fabrication method for a spacer composed of pillar structures can be adopted as a wall plate fabrication method. The same material as that for a spacer composed of pillar structures can be adopted as the material for a wall plate.

<Specifications of Spacer Composed of Pillar Structures>

If a spacer is composed of a plurality of pillar structures, an interval for and the shapes of the pillar structures are determined in the manner below.

<Interval Between Pillar Structures>

The interval between pillar structures is appropriately set in accordance with the diameter of a biological sample. In terms of achieving higher sensitivity, that is, minimizing blocking of diffusion of a dissolved substance around a biological sample by pillar structures, a wider interval is more preferable for the pillar structures.

The intervals between pillar structures need not be uniform. There may be a region where pillar structures are densely present and a region where pillar structures are sparsely present or there may be a region where no pillar structures are present.

For example, a structure in which no pillar structure is formed only in a region immediately above an electrode surface and a biological sample is held only by pillar structures around the electrode surface effectively prevents blocking of diffusion of a dissolved substance immediately below the biological sample and achieves higher sensitivity.

<Diameter of Pillar Structure>

The diameter of each pillar structure is large enough to secure strength that allows holding of a biological sample away from an electrode surface. Note that a smaller diameter is more preferable for pillar structures in terms of achieving higher sensitivity, that is, minimizing blocking of diffusion of a dissolved substance around a biological sample by the pillar structures.

<Upper Surface Shape of Pillar Structure>

There are no restrictions on the shape of an upper surface of a pillar structure. The shape of the upper surface of the pillar structure may be circular or polygonal (for example, triangular or quadrangular).

In a pillar structure, the shape of an upper surface and that of a lower surface need not be identical. The area of the upper surface and that of the lower surface need not be identical in the pillar structure. For example, the area of the upper surface may be intentionally reduced (that is, a tapered pillar structure may be formed) by changing etching conditions for an insulating layer at the time of pillar structure creation.

If a biological sample is cells, a piece of tissue, or the like, a tapered pillar structure can reduce a contact area and adhesivity between the biological sample and pillar structures. The tapered pillar structure reduces force needed to peel the biological sample at the time of removal of the biological sample after measurement, which results in reduction of damage to the biological sample.

<Specifications of Wall Plate Functioning as Spacer>

If a spacer is composed of a plurality of wall plates, an interval for and the shapes of the wall plates are determined in the manner below.

<Interval Between Wall Plates>

The interval between wall plates is appropriately set in accordance with the diameter of a biological sample. In terms of achieving higher sensitivity, that is, minimizing blocking of diffusion of a dissolved substance around a biological sample by wall plates, a wider interval is more preferable for the wall plates.

For example, no wall plate is formed in a region immediately above an electrode surface, and the electrode surface is sandwiched between wall plates. This effectively prevents blocking of diffusion of a dissolved substance immediately below a biological sample and allows effective reduction of crosstalk.

<Thickness of Wall Plate>

The thickness of each wall plate is large enough to secure strength that allows holding of a biological sample away from an electrode surface.

<Shape of Wall Plate>

The shape of an upper surface and that of a lower surface in a wall plate need not be identical. The area of the upper surface and that of the lower surface in the wall plate need not be identical. For example, the area of the upper surface may be intentionally reduced (that is, a tapered wall plate may be formed) by changing etching conditions for an insulating layer at the time of wall plate creation.

If a biological sample is cells, a piece of tissue, or the like, a tapered wall plate can reduce a contact area and adhesivity between the biological sample and wall plates. The tapered wall plate reduces force needed to peel the biological sample at the time of removal of the biological sample after measurement, which results in reduction of damage to the biological sample.

<Transducer>

Figure 14A:
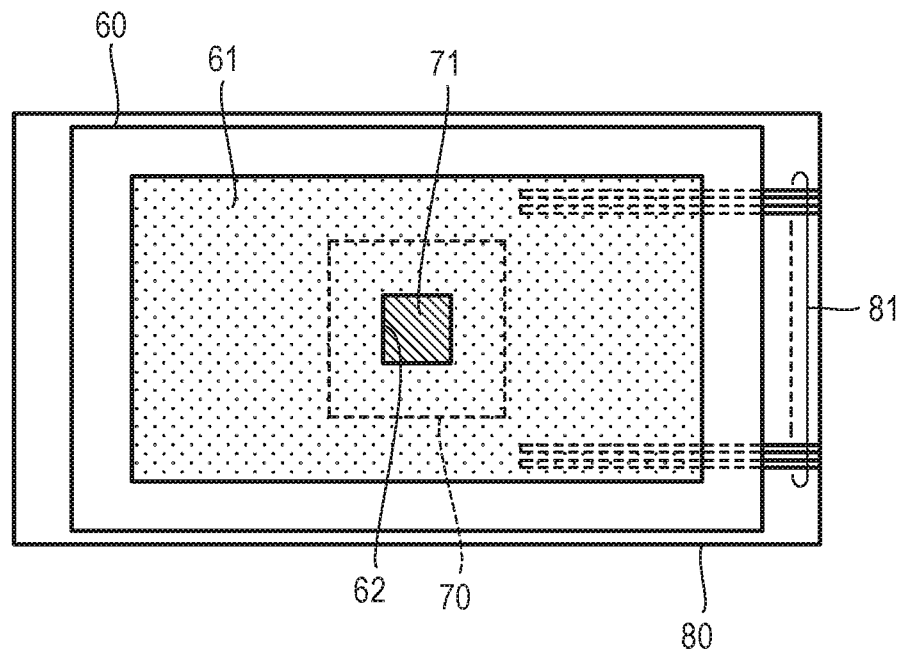
FIG. 14A is a plan view showing one embodiment of a transducer according to the present invention.
Figure 14B:
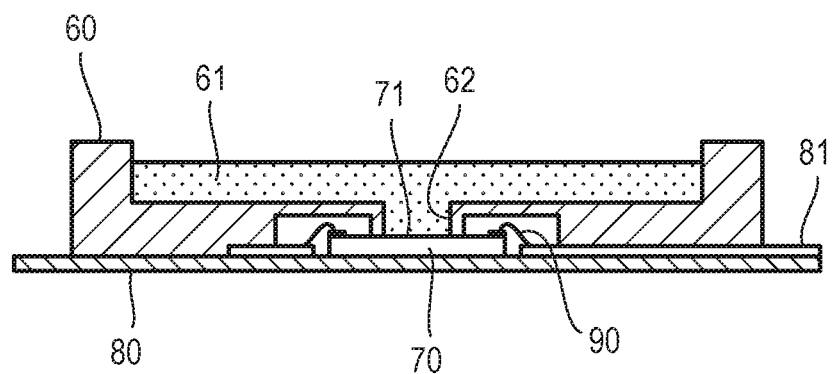
FIG. 14B is a cross-sectional view showing the one embodiment of the transducer according to the present invention.
Figure 15:
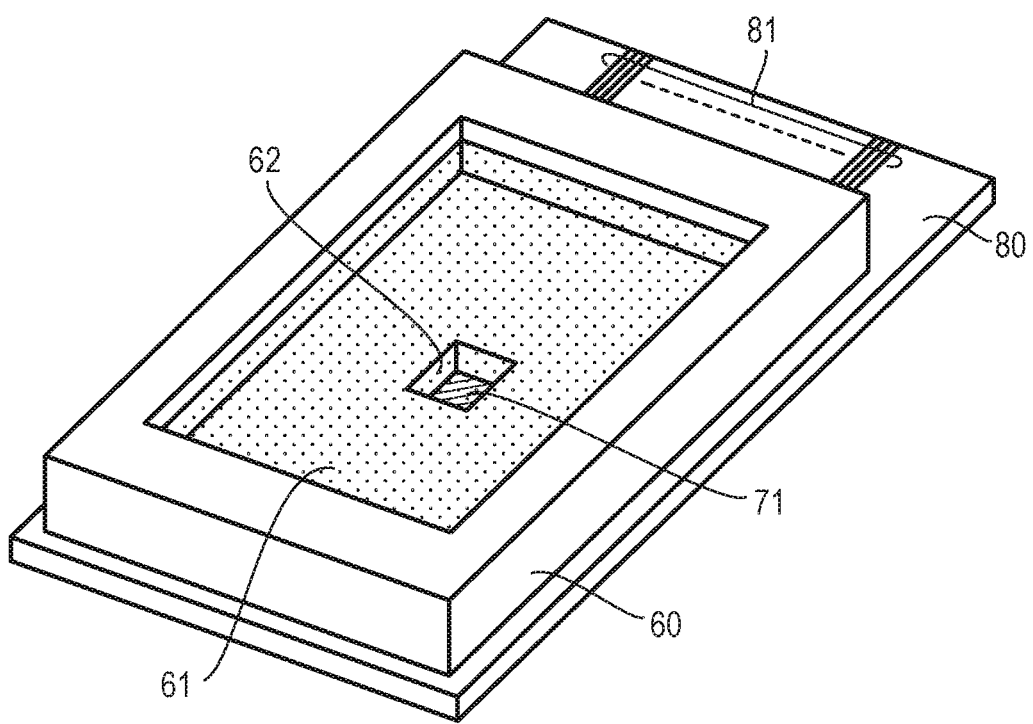
FIG. 15 is a perspective view of the transducer shown in FIG. 14.

An example of a specific configuration of a transducer according to the present invention will next be described with reference to FIGS. 14 and 15. The transducer is used for electrochemical measurement of a chemical substance generated or consumed in a biological sample.

The transducer is configured such that a solution well 60 is mounted on an LSI chip 70. The solution well 60 contains a solution 61 and a biological sample which is immersed in the solution 61. A hole 62 is formed at the center of the solution well 60. The LSI chip 70 is arranged at a lower end of the hole 62. The hole 62 is closed by the LSI chip 70.

The LSI chip 70 and the solution well 60 are fixed on a substrate 80. A pattern 81 of many conductors for connection with an external device which controls the transducer is formed on the substrate 80. Reference numeral 90 in FIG. 14B indicates bonding wires which interconnect the LSI chip 70 and the pattern 81 of conductors.

A sensor region 71 is formed on an upper surface of the LSI chip 70. In FIG. 14A, the sensor region 71 is indicated by hatching. The sensor region 71 is located in the hole 62 at a bottom surface of the solution well 60. Although not shown, a plurality of electrodes (working electrodes) are formed in the sensor region 71 in this example, and a spacer composed of pillar structures is also formed in the sensor region 71. A wall plate is formed between adjacent ones of the working electrodes. The LSI chip 70 has a function of applying a voltage to the working electrodes, a function of detecting a reaction at each working electrode as a current value and amplifying the current value, and the like. The spacer and the wall plate are as described earlier.

As described above, a biological sample is away by a desirable distance from a flat surface with an electrode surface arranged thereon by a spacer or a plurality of wall plates. Thus, a three-dimensional region, through which a dissolved substance in a solution can diffuse, is secured, and a sufficient amount of the dissolved substance is supplied to the biological sample.

According to the present invention, the amount of a chemical substance to be detected by a working electrode increases, and measurement sensitivity is higher than conventional electrochemical measurement that performs measurement with a biological sample located close to an electrode surface.

A perpendicular distance between a working electrode and a biological sample may vary depending on the shape and surface state of the biological sample. However, placing a biological sample at a desirable distance from an electrode surface allows reduction of the influence of differences in a diffusion distance of a chemical substance which are associated with differences in a perpendicular distance between a working electrode and the biological sample, which makes comparability and reproducibility of measurement higher than conventional electrochemical measurement.

According to the present invention, a wall plate which is formed between adjacent electrode surfaces and is impervious to a dissolved substance in a solution reduces sensing crosstalk between electrode surfaces due to diffusion of a chemical substance to be detected in the solution.

For example, in the case of simultaneous evaluation of a plurality of biological samples, the influence of a distant sample on a current value at each working electrode can be prevented. This improves the quantitativity of biological sample evaluation. Since the interval between electrode surfaces can be narrowed, the cost of substrates can be reduced.

An electrochemical measurement device and a transducer according to the present invention will be described from a different standpoint in the manner below. Note that the following description does not conflict with the disclosed matters described in the "MEANS TO SOLVE THE PROBLEMS" and that the following description and the "MEANS TO SOLVE THE PROBLEMS" can refer to each other.

Item 1

An electrochemical measurement device for measuring a chemical substance generated or consumed in a biological sample in a solution, including:

a solution well for containing the solution and the biological sample;

two or more electrode surfaces, each of the electrode surfaces being a surface of an electrode which is in contact with the solution while the solution well contains the solution, and an oxidation-reduction reaction progressing between each electrode surface and the chemical substance;

a spacer; and at least one wall plate, wherein the two or more electrode surfaces, the spacer, and the at least one wall plate are arranged on a bottom surface of the solution well, a diameter $d_{el}$ of each of the two or more electrode surfaces is not more than 80 µm, a height of the spacer has a predetermined value within a range for h given by equation (c1):

$$h = \frac{21.8(d_{el} + 0.8)}{d_{el} + 9.7} \pm 5 [\mu m], \qquad (c1)$$

the spacer has a structure in which an enclosed three-dimensional region is not formed by the biological sample, the bottom surface, and the spacer while the biological sample is in contact with the spacer, the at least one wall plate has a property of being impervious to a dissolved substance in the solution, the at least one wall plate has a height not less than the height of the spacer, and at least two electrode surfaces of the two or more electrode surfaces are separated by the at least one wall plate.

Item 2

An electrochemical measurement device for measuring a chemical substance generated or consumed in a biological sample in a solution, including:

a solution well for containing the solution and the biological sample;

two or more electrode surfaces, each of the electrode surfaces being a surface of an electrode which is in contact with the solution while the solution well contains the solution, and an oxidation-reduction reaction progressing between each electrode surface and the chemical substance;

a spacer; and at least one wall plate, wherein the two or more electrode surfaces, the spacer, and the at least one wall plate are arranged on a bottom surface of the solution well, a diameter $d_{el}$ of each of the two or more electrode surfaces is not more than 80 µm, a height of the spacer at a position at a distance m, which is a distance in a direction parallel to the bottom surface from a center of one electrode surface of the two or more electrode surfaces, from the center of the one electrode surface has a predetermined value within a range for h given by equation (c2):

$$h = \sqrt{(1.05 d_{el} + 6.89)m} - 0.48 d_{el} - 2.38 \pm 5 \; [\mu m] \qquad (c2)$$

where 0<m≤L/2 and h>0 hold, L being a distance between the center of the one electrode surface and a center of a different electrode surface of the two or more electrode surfaces which is closest to the one electrode surface, the spacer has a structure in which an enclosed three-dimensional region is not formed by the biological sample, the bottom surface, and the spacer while the biological sample is in contact with the spacer, the at least one wall plate has a property of being impervious to a dissolved substance in the solution, the at least one wall plate has a height not less than the height of the spacer, and at least two electrode surfaces of the two or more electrode surfaces are separated by the at least one wall plate.

Item 3

In the electrochemical measurement device according to item 1 or item 2, the two or more electrode surfaces include three or more electrode surfaces, the at least one wall plate includes two or more wall plates, at least two electrode surfaces of the three or more electrode surfaces are arranged in at least one of at least one or more portions, the at least one or more portions being at least one or more portions of the bottom surface which are located between adjacent two of the two or more wall plates or at least one or more portions of the bottom surface which are located between one wall plate of the two or more wall plates and a side wall of the solution well.

Item 4

In the electrochemical measurement device according to any one of item 1 to item 3, the spacer is composed of pillar structures, and each of pillar structures extends in a normal direction of the flat surface.

Item 5

In the electrochemical measurement device according to any one of item 1 to item 3, the spacer is a porous structure.

Item 6

An electrochemical measurement device for measuring a chemical substance generated or consumed in a biological sample in a solution, including:

a solution well for containing the solution and the biological sample;

two or more electrode surfaces, each of the electrode surfaces being a surface of an electrode which is in contact with the solution while the solution well contains the solution, and an oxidation-reduction reaction progressing between each electrode surface and the chemical substance; and two or more wall plates, wherein the two or more electrode surfaces and the two or more wall plates are arranged on a bottom surface of the solution well, a diameter $d_{el}$ of each of the two or more electrode surfaces is not more than 80 μm, respective heights of the two or more wall plates have predetermined values within a range for h given by equation (c3):

$$h = \frac{21.8(d_{el} + 0.8)}{d_{el} + 9.7} \pm 5 [\mu m], \quad (c3)$$

a structure of each of the two or more wall plates does not form an enclosed three-dimensional region together with the biological sample and the bottom surface, being in contact with the biological sample, the two or more wall plates each have a property of being impervious to a dissolved substance in the solution, and at least two electrode surfaces of the two or more electrode surfaces are separated by at least one wall plate of the two or more wall plates.

Item 7

An electrochemical measurement device for measuring a chemical substance generated or consumed in a biological sample in a solution, including:

a solution well for containing the solution and the biological sample;

two or more electrode surfaces, each of the electrode surfaces being a surface of an electrode which is in contact with the solution while the solution well contains the solution, and an oxidation-reduction reaction progressing between each electrode surface and the chemical substance; and two or more wall plates, wherein the two or more electrode surfaces and the two or more wall plates are arranged on a bottom surface of the solution well, a diameter $d_{el}$ of each of the two or more electrode surfaces is not more than 80 μm, a height of one wall plate at a position at a distance m, which is a distance in a direction parallel to the bottom surface from a center of one electrode surface of the two or more electrode surfaces, from the center of the one electrode surface of the two or more wall plates has a predetermined value within a range for h given by equation (c4):

$$h = \sqrt{(1.05 d_{el} + 6.89) m} - 0.48 d_{el} - 2.38\ 35\ 5\ [\mu m], \quad (c4)$$

where 0<m≤L/2 and h>0 hold, L being a distance between the center of the one electrode surface and a center of a different electrode surface of the two or more electrode surfaces which is closest to the one electrode surface, a structure of each of the two or more wall plates does not form an enclosed three-dimensional region together with the biological sample and the bottom surface, being in contact with the biological sample, the two or more wall plates each have a property of being impervious to a dissolved substance in the solution, and at least two electrode surfaces of the two or more electrode surfaces are separated by at least one wall plate of the two or more wall plates.

Item 8

In the electrochemical measurement device according to item 6 or item 7, a depression is formed at an upper portion of at least one of two wall plates of the two or more wall plates, the depression being located next to one electrode surface of the two or more electrode surfaces when the bottom surface is squarely viewed, the two wall plates being located on two sides of the one electrode surface.

Item 9

In the electrochemical measurement device according to any one of item 6 to item 8, a recess which increases an interval between two wall plates of the two or more wall plates is formed at at least one of the two wall plates, the recess being located next to one electrode surface of the two or more electrode surfaces when the bottom surface is squarely viewed and extending in a normal direction of the bottom surface, the two wall plates being located on two sides of the one electrode surface.

Item 10

The electrochemical measurement device according to any one of item 6 to item 9, including
a partition plate which is a wall plate having a height more than a maximum value for the heights of the two or more wall plates, wherein
the partition plate has a property of being impervious to the dissolved substance in the solution, and
at least two electrode surfaces of the two or more electrode surfaces are separated by the partition plate.

Item 11

A transducer including:
an electrochemical measurement device according to any one of item 1 to item 10; and
an integrated circuit, wherein
the bottom surface of the solution well is a surface of the integrated circuit.

What is claimed is:

1. An electrochemical measurement device comprising a plurality of working electrodes, each of the plurality of working electrodes including an electrode surface supplying or receiving electrons to or from a chemical substance generated or consumed in a biological sample in a solution to cause an oxidation-reduction reaction, wherein
all of the electrode surfaces have diameter dimensions $d_{el}$ not more than 80 μm and are arrayed on one flat surface,
a spacer is provided in a solution well containing the solution and the biological sample, the spacer having an inverse-cone-shaped profile surface at a distance $h_2$ in a direction perpendicular to the one flat surface, the distance $h_2$ being dependent on a distance m in a direction parallel to the one flat surface from a center of the closest electrode surface and satisfying $$h_2 = [(1.05 d_{el} + 6.89)m]^{1/2} - 0.48 d_{el} - 2.38 \pm 5 \, [\mu m],$$

the spacer inhibiting the biological sample from entering a region on a side with the one flat surface of the profile surface and allowing a dissolved substance in the solution to diffuse, and
a wall plate is provided between the at least two electrode surfaces adjacent to each other, the wall plate extending to cross a line connecting centers of the at least two electrode surfaces, having a height not less than a maximum height of the spacer from the one flat surface, and being impervious to the dissolved substance in the solution.

2. The electrochemical measurement device according to claim 1, wherein
the electrode surfaces are arrayed in a configuration in which a plurality of electrode rows are arranged in a second direction orthogonal to a first direction, each of the plurality of electrode rows having the plurality of the electrode surfaces which are arranged in a straight line in the first direction, and
the wall plate is provided to extend in the first direction between the electrode rows adjacent to each other.

3. The electrochemical measurement device according to claim 1, wherein
the spacer is composed of a group of pillar structures which extend in the direction perpendicular to the one flat surface and stand at intervals less than 100 μm.

4. The electrochemical measurement device according to claim 1, wherein
the spacer is composed of a porous structure having a pore diameter less than 100 μm.

5. An electrochemical measurement device comprising a plurality of working electrodes, each of the plurality of working electrodes including an electrode surface supplying or receiving electrons to or from a chemical substance generated or consumed in a biological sample in a solution to cause an oxidation-reduction reaction, wherein:
all of the electrode surfaces have diameter dimensions $d_{el}$ not more than 80 μm and are arrayed on one flat surface, on which x-y orthogonal coordinates are defined, such that x coordinates of centers of the at least two electrode surfaces are different from each other,
a plurality of wall plates are provided to be arrayed at intervals less than 100 μm in an x direction on the one flat surface where the electrode surfaces are arrayed, each of the plurality of wall plates extending in a y direction, having a height $h_3$ satisfying $$h_3 = 21.8(d_{el} + 0.8)/(d_{el} + 0.97) \pm 5 \, [\mu m],$$

and being impervious to a dissolved substance in the solution, and
the height $h_3$ of at least one of two of the wall plates, distances in the x direction of which from a center of one of the electrode surfaces are smallest and second smallest, changes along the y direction so as to be minimal at a y coordinate equal to a y coordinate of the center of the electrode surface.

6. An electrochemical measurement device comprising a plurality of working electrodes, each of the plurality of working electrodes including an electrode surface supplying or receiving electrons to or from a chemical substance generated or consumed in a biological sample in a solution to cause an oxidation reduction reaction, wherein
all of the electrode surfaces have diameter dimensions $d_{el}$ not more than 80 μm and are arrayed on one flat surface, on which x-y orthogonal coordinates are defined, such that x coordinates of centers of the at least two electrode surfaces are different from each other,
a plurality of wall plates are provided to be arrayed at intervals less than 100 μm in an x direction on the one flat surface where the electrode surfaces are arrayed, each of the plurality of wall plates extending in a y direction, having a height $h_3$ satisfying $$h_3 = 21.8(d_{el} + 0.8)/(d_{el} + 0.97) \pm 5 \, [\mu m],$$

and being impervious to a dissolved substance in the solution, and
the heights $h_3$ of two of the wall plates which extend on two outer sides of one of the electrode surfaces and are parallel to each other without a different one of the wall plates sandwiched between the two wall plates change along the y direction so as to be minimal at y coordinates equal to a y coordinate of a center of the electrode surface.

7. An electrochemical measurement device comprising a plurality of working electrodes, each of the plurality of working electrodes including an electrode surface supplying or receiving electrons to or from a chemical substance generated or consumed in a biological sample in a solution to cause an oxidation-reduction reaction, wherein
all of the electrode surfaces have diameter dimensions $d_{el}$ not more than 80 μm and are arrayed on one flat surface, on which x-y orthogonal coordinates are defined, such that x coordinates of centers of the at least two electrode surfaces are different from each other,
a plurality of wall plates are provided to be arrayed at intervals less than 100 μm in an x direction on the one flat surface where the electrode surfaces are arrayed, each of the plurality of wall plates extending in a y direction, having a height $h_3$ satisfying $$h_3=21.8(d_{el}+0.8)/(d_{el}+0.97)\pm 5\ [\mu m],$$

and being impervious to a dissolved substance in the solution, and an x coordinate of at least one of two of the wall plates, distances in the x direction of which from a center of one of the electrode surfaces are smallest and second smallest, changes locally along the y direction such that the distance in the x direction from the center of the electrode surface is maximal at a y coordinate equal to a y coordinate of the center of the electrode surface.

8. An electrochemical measurement device comprising a plurality of working electrodes, each of the plurality of working electrodes including an electrode surface supplying or receiving electrons to or from a chemical substance generated or consumed in a biological sample in a solution to cause an oxidation-reduction reaction, wherein all of the electrode surfaces have diameter dimensions $d_{el}$ not more than 80 μm and are arrayed on one flat surface, on which x-y orthogonal coordinates are defined, such that x coordinates of centers of the at least two electrode surfaces are different from each other, a plurality of wall plates are provided to be arrayed at intervals less than 100 μm in an x direction on the one flat surface where the electrode surfaces are arrayed, each of the plurality of wall plates extending in a y direction, having a height $h_3$ satisfying $$h_3=21.8(d_{el}+0.8)/(d_{el}+0.97)\pm 5\ [\mu m],$$

and being impervious to a dissolved substance in the solution, and an x coordinate of a first wall plate which is one of the wall plates, a distance in the x direction of which from a center of one of the electrode surfaces is smallest, changes locally along the y direction such that the distance in the x direction from the center of the electrode surface is maximal at a y coordinate equal to a y coordinate of the center of the electrode surface, and an x coordinate of a second wall plate which is a different one of the wall plates which is adjacent to the first wall plate across the center of the electrode surface changes locally along the y direction such that a distance in the x direction from the center of the electrode surface is maximal at a y coordinate equal to the y coordinate of the center of the electrode surface.

9. An electrochemical measurement device comprising a plurality of working electrodes, each of the plurality of working electrodes including an electrode surface supplying or receiving electrons to or from a chemical substance generated or consumed in a biological sample in a solution to cause an oxidation-reduction reaction, wherein all of the electrode surfaces have diameter dimensions $d_{el}$ not more than 80 μm and are arrayed on one flat surface, on which x-y orthogonal coordinates are defined, in a configuration in which a plurality of electrode rows are arranged in an x direction, each of the plurality of electrode rows having one or more of the electrode surfaces which are arranged in a y direction such that x coordinates of centers of all of the one or more electrode surfaces match up, and a plurality of first wall plates are provided to be arrayed at intervals less than 100 μm in the x direction on the one flat surface where the electrode surfaces are arrayed, the plurality of first wall plates extending in the y direction, having heights $h_4$, and being impervious to a dissolved substance in the solution, the heights $h_4$ being dependent on a distance m in the x direction from a center of one of the electrode surfaces which belongs to the electrode row that is closest in the x direction and satisfying $$h_4=[(1.05d_{el}+6.89)m]^{1/2}-0.48d_{el}-2.38\pm 5\ [\mu m]$$

and changing gradually.

10. The electrochemical measurement device according to claim 9, wherein the height $h_4$ of at least one of one or more of the wall plates which each extend to cross a line segment connecting a first end point and a second end point over a whole or part of a width of the wall plate changes along the y direction so as to be minimal at a y coordinate equal to a y coordinate of a center of one of the electrode surfaces, the first end point being not a relatively farther one of a point 300 μm away in one direction of the x direction from the center of the electrode surface and a point at a distance which is one-half of a distance to an x coordinate of a center of the electrode surface which belongs to the electrode row that is adjacent in the one direction, the second end point being not a relatively farther one of a point 300 μm away in the other direction of the x direction from the center of the electrode surface and a point at a distance which is one-half of a distance to an x coordinate of a center of the electrode surface which belongs to the electrode row that is adjacent in the other direction.

11. The electrochemical measurement device according to claim 10, wherein the heights $h_4$ of all of one or more of the wall plates which each extend to cross the line segment over the whole of the widths of the wall plates change along the y direction so as to be minimal at y coordinates equal to the y coordinate of the center of the electrode surface.

12. The electrochemical measurement device according to claim 9, wherein a second wall plate is further provided between at least one combination of the electrode rows which are adjacent to each other in the x direction, the second wall plate extending in the y direction at an x coordinate intermediate between x coordinates of centers of the electrode surfaces which belong to the two electrode rows, having a height more than a maximum height of the wall plates, and being impervious to the dissolved substance in the solution.

13. A transducer in which a solution well capable of containing a solution and a biological sample immersed in the solution is mounted on a large-scale integration chip, and a plurality of working electrodes that each include an electrode surface supplying or receiving electrons to or from a chemical substance generated or consumed in the biological sample in the solution to cause an oxidation-reduction reaction are provided on the large-scale integration chip, wherein all of the electrode surfaces have diameter dimensions $d_{el}$ not more than 80 μm and are arrayed on one flat surface, a spacer is provided in the solution well, the spacer having an inverse-cone-shaped profile surface at a distance $h_2$ in a direction perpendicular to the one flat surface, the distance $h_2$ being dependent on a distance m in a direction parallel to the one flat surface from a center of the closest electrode surface and satisfying $$h_2=[(1.05d_{el}+6.89)m]^{1/2}-0.48d_{el}-2.38\pm 5\ [\mu m],$$

the spacer inhibiting the biological sample from entering a region on a side with the one flat surface of the profile surface and allowing a dissolved substance in the solution to diffuse, and a wall plate is provided between the at least two electrode surfaces adjacent to each other, the wall plate extending to cross a line connecting centers of the at least two electrode surfaces, having a height not less than a maximum height of the spacer from the one flat surface, and being impervious to the dissolved substance in the solution.

14. The transducer according to claim 13, wherein
the electrode surfaces are arrayed in a configuration in which a plurality of electrode rows are arranged in a second direction orthogonal to a first direction, each of the plurality of electrode rows having the plurality of the electrode surfaces which are arranged in a straight line in the first direction, and the wall plate is provided to extend in the first direction between the electrode rows adjacent to each other.

15. The transducer according to claim 13, wherein
the spacer is composed of a group of pillar structures which extend in the direction perpendicular to the one flat surface and stand at intervals less than 100 µm.

16. The transducer according to claim 13, wherein
the spacer is composed of a porous structure having a pore diameter less than 100 µm.

17. A transducer in which a solution well capable of containing a solution and a biological sample immersed in the solution is mounted on a large-scale integration chip, and a plurality of working electrodes that each include an electrode surface supplying or receiving electrons to or from a chemical substance generated or consumed in the biological sample in the solution to cause an oxidation-reduction reaction are provided on the large-scale integration chip, wherein all of the electrode surfaces have diameter dimensions $d_{el}$ not more than 80 µm and are arrayed on one flat surface, on which x-y orthogonal coordinates are defined, such that x coordinates of centers of the at least two electrode surfaces are different from each other, a plurality of wall plates are provided to be arrayed at intervals less than 100 µm in an x direction on the one flat surface where the electrode surfaces are arrayed, each of the plurality of wall plates extending in a y direction, having a height $h_3$ satisfying $h_3=21.8(d_{el}+0.8)/(d_{el}+0.97)\pm5$ [µm], and being impervious to a dissolved substance in the solution, and the height $h_3$ of at least one of two of the wall plates, distances in the x direction of which from a center of one of the electrode surfaces are smallest and second smallest, changes along the y direction so as to be minimal at a y coordinate equal to a y coordinate of the center of the electrode surface.

18. A transducer in which a solution well capable of containing a solution and a biological sample immersed in the solution is mounted on a large-scale integration chip, and a plurality of working electrodes that each include an electrode surface supplying or receiving electrons to or from a chemical substance generated or consumed in the biological sample in the solution to cause an oxidation-reduction reaction are provided on the large-scale integration chip, wherein all of the electrode surfaces have diameter dimensions $d_{el}$ not more than 80 µm and are arrayed on one flat surface, on which x-y orthogonal coordinates are defined, such that x coordinates of centers of the at least two electrode surfaces are different from each other, a plurality of wall plates are provided to be arrayed at intervals less than 100 µm in an x direction on the one flat surface where the electrode surfaces are arrayed, each of the plurality of wall plates extending in a y direction, having a height $h_3$ satisfying $h_3=21.8(d_{el}+0.8)/(d_{el}+0.97)\pm5$ [µm], and being impervious to a dissolved substance in the solution, and the heights $h_3$ of two of the wall plates which extend on two outer sides of one of the electrode surfaces and are parallel to each other without a different one of the wall plates sandwiched between the two wall plates change along the y direction so as to be minimal at y coordinates equal to a y coordinate of a center of the electrode surface.

19. A transducer in which a solution well capable of containing a solution and a biological sample immersed in the solution is mounted on a large-scale integration chip, and a plurality of working electrodes that each include an electrode surface supplying or receiving electrons to or from a chemical substance generated or consumed in the biological sample in the solution to cause an oxidation-reduction reaction are provided on the large-scale integration chip, wherein all of the electrode surfaces have diameter dimensions $d_{el}$ not more than 80 µm and are arrayed on one flat surface, on which x-y orthogonal coordinates are defined, such that x coordinates of centers of the at least two electrode surfaces are different from each other, a plurality of wall plates are provided to be arrayed at intervals less than 100 µm in an x direction on the one flat surface where the electrode surfaces are arrayed, each of the plurality of wall plates extending in a y direction, having a height $h_3$ satisfying $h_3=21.8(d_{el}+0.8)/(d_{el}+0.97)\pm5$ [µm], and being impervious to a dissolved substance in the solution, and an x coordinate of at least one of two of the wall plates, distances in the x direction of which from a center of one of the electrode surfaces are smallest and second smallest, changes locally along the y direction such that the distance in the x direction from the center of the electrode surface is maximal at a y coordinate equal to a y coordinate of the center of the electrode surface.

20. A transducer in which a solution well capable of containing a solution and a biological sample immersed in the solution is mounted on a large-scale integration chip, and a plurality of working electrodes that each include an electrode surface supplying or receiving electrons to or from a chemical substance generated or consumed in the biological sample in the solution to cause an oxidation-reduction reaction are provided on the large-scale integration chip, wherein all of the electrode surfaces have diameter dimensions $d_{el}$ not more than 80 µm and are arrayed on one flat surface, on which x-y orthogonal coordinates are defined, such that x coordinates of centers of the at least two electrode surfaces are different from each other, a plurality of wall plates are provided to be arrayed at intervals less than 100 µm in an x direction on the one flat surface where the electrode surfaces are arrayed, each of the plurality of wall plates extending in a y direction, having a height $h_3$ satisfying $$h_3 = 21.8(d_{el}+0.8)/(d_{el}+0.97) \pm 5 \ [\mu m],$$

and being impervious to a dissolved substance in the solution, and an x coordinate of a first wall plate which is one of the wall plates, a distance in the x direction of which from a center of one of the electrode surfaces is smallest, changes locally along the y direction such that the distance in the x direction from the center of the electrode surface is maximal at a y coordinate equal to a y coordinate of the center of the electrode surface, and an x coordinate of a second wall plate which is a different one of the wall plates which is adjacent to the first wall plate across the center of the electrode surface changes locally along the y direction such that a distance in the x direction from the center of the electrode surface is maximal at a y coordinate equal to they coordinate of the center of the electrode surface.

21. A transducer in which a solution well capable of containing a solution and a biological sample immersed in the solution is mounted on a large-scale integration chip, and a plurality of working electrodes that each include an electrode surface supplying or receiving electrons to or from a chemical substance generated or consumed in the biological sample in the solution to cause an oxidation-reduction reaction are provided on the large-scale integration chip, wherein all of the electrode surfaces have diameter dimensions $d_{el}$ not more than 80 μm and are arrayed on one flat surface, on which x-y orthogonal coordinates are defined, in a configuration in which a plurality of electrode rows are arranged in an x direction, each of the plurality of electrode rows having one or more of the electrode surfaces which are arranged in a y direction such that x coordinates of centers of all of the one or more electrode surfaces match up, and a plurality of first wall plates are provided to be arrayed at intervals less than 100 μm in the x direction on the one flat surface where the electrode surfaces are arrayed, the plurality of first wall plates extending in the y direction, having heights $h_4$, and being impervious to a dissolved substance in the solution, the heights $h_4$ being dependent on a distance m in the x direction from a center of one of the electrode surfaces which belongs to the electrode row that is closest in the x direction and satisfying $$h_4 = [(1.05 d_{el}+6.89)m]^{1/2} - 0.48 d_{el} - 2.38 \pm 5 \ [\mu m]$$

and changing gradually.

22. The transducer according to claim 21, wherein
the height $h_4$ of at least one of one or more of the wall plates which each extend to cross a line segment connecting a first end point and a second end point over a whole or part of a width of the wall plate changes along the y direction so as to be minimal at a y coordinate equal to a y coordinate of a center of one of the electrode surfaces, the first end point being not a relatively farther one of a point 300 μm away in one direction of the x direction from the center of the electrode surface and a point at a distance which is one-half of a distance to an x coordinate of a center of the electrode surface which belongs to the electrode row that is adjacent in the one direction, the second end point being not a relatively farther one of a point 300 μm away in the other direction of the x direction from the center of the electrode surface and a point at a distance which is one-half of a distance to an x coordinate of a center of the electrode surface which belongs to the electrode row that is adjacent in the other direction.

23. The transducer according to claim 22, wherein
the heights $h_4$ of all of one or more of the wall plates which each extend to cross the line segment over the whole of the widths of the wall plates change along the y direction so as to be minimal at y coordinates equal to the y coordinate of the center of the electrode surface.

24. The transducer according to claim 21, wherein
a second wall plate is further provided between at least one combination of the electrode rows which are adjacent to each other in the x direction, the second wall plate extending in the y direction at an x coordinate intermediate between x coordinates of centers of the electrode surfaces which belong to the two electrode rows, having a height more than a maximum height of the wall plates, and being impervious to the dissolved substance in the solution.

* * * * *